United States Patent [19]
Miki et al.

[11] Patent Number: 5,985,875
[45] Date of Patent: Nov. 16, 1999

[54] 1,2,4-TRIAZINE-3, 5-DIONE DERIVATIVES, THEIR PRODUCTION AND USE THEREOF

[75] Inventors: Hideki Miki, Osaka; Isao Aoki, Hyogo; Koichi Iwanaga, Osaka; Toshikatsu Hayashi, Kyoto, all of Japan

[73] Assignee: Takeda Chemical Industries, Ltd., Osaka, Japan

[21] Appl. No.: 08/921,047

[22] Filed: Aug. 29, 1997

[30] Foreign Application Priority Data

Aug. 30, 1996 [JP] Japan .................................. 8-230434

[51] Int. Cl.[6] ........................ A61K 31/53; C07D 253/075
[52] U.S. Cl. ............................................ 514/242; 544/182
[58] Field of Search .............................. 544/182; 514/242

[56] References Cited

U.S. PATENT DOCUMENTS

| | | | |
|---|---|---|---|
| 3,883,527 | 5/1975 | Brennan | 260/248 |
| 3,883,528 | 5/1975 | Mylari | 260/248 |
| 3,896,124 | 7/1975 | Mylari | 260/248 |
| 3,905,971 | 9/1975 | Miller | 260/247.5 |
| 3,912,723 | 10/1975 | Miller | 260/239.7 |
| 4,782,056 | 11/1988 | Rosner et al. | 514/242 |
| 5,141,938 | 8/1992 | Lindner et al. | 514/242 |
| 5,188,832 | 2/1993 | Mehlhorn et al. | 424/405 |
| 5,256,631 | 10/1993 | Lindner et al. | 504/229 |

FOREIGN PATENT DOCUMENTS

| | | |
|---|---|---|
| 0 232 932 | 8/1987 | European Pat. Off. |
| 0 648 760 | 4/1995 | European Pat. Off. |
| 0 737 672 | 10/1996 | European Pat. Off. |
| 0 737 672 A2 | 10/1996 | European Pat. Off. |

OTHER PUBLICATIONS

Carroll, R "Anticoccidial Derivatives of 6–Azauracil. 5. Potentiation by Benzophenone Side Chains" J. Med. Chem. 1983, 26, 96–100.

Miki et al, Chemical Abstracts, vol. 127 (Jul. 21, 1997).

Mylari et al., "Anticoccidial Derivatives of 6–Azauracil. 1. Enhancement of Activity by Benzylation of Nitrogen–1. Observation on the Design of Nucelotide Analogues in Chemotherapy" J. Med. Chem. 20:475–483 (1979).

Miller et al., "Anticoccidial Derivatives of 6–Azauracil. 2. High Potency and Long Plasma Life of N1–Phenyl Structures[1a]" J. Med. Chem. 22:1483–1487 (1979).

Miller et al., "Anticoccidial Derivatives of 6–Azauracil. 3. Synthesis, High Activity, and Short Plasma Half–life of 1–Phenyl–6–azauracils Containing Sulfonamide Substituents" J. Med. Chem. 23:1083–1087 (1980).

Miller et al., "Anticoccidial Derivatives of 6–Azauracil. 4. A 1000–fold Enhancement of Potency by Phenyl Sulfide and Phenyl Sulfone Side Chains[1]" J. Med. Chem. 24:1337–1342 (1981).

Shin Jikken Kagaku Koza, vol. 15(II), 88–93, 206–207, 323–325 and 444–447, 1977.

J.W. McFarland, et al., J. Med., Chem., 34, 1908–1911, 1991.

Monatshefte fur Chemie, 94, 258–262, 1963.

Primary Examiner—Richard L. Raymond
Attorney, Agent, or Firm—Foley & Lardner

[57] ABSTRACT

The present invention relates to compounds represented by the formula:

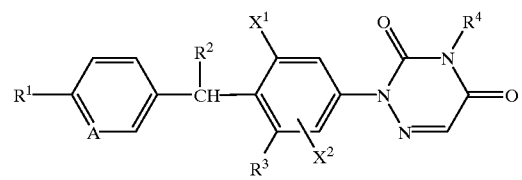

wherein $R^1$ is (1) an optionally substituted alkyl group which may be bonded through a hetero atom, (2) an optionally substituted acyl group, (3) an alkylsulfonyl group, (4) an alkylsulfinyl group, or (5) an optionally substituted sulfamoyl group; A is $-N=$ or $-CH=$; $R^2$ is a hydrogen atom or an alkyl group which may optionally be substituted with halogen and which may be bonded through a hetero atom;

$X^1$ is halogen or a lower alkyl group;

$X^2$ is a hydrogen atom or a fluorine atom;

$R^3$ is a hydrogen atom, halogen or a lower alkyl group;

and $R^4$ is a hydrogen atom, an optionally substituted alkyl group or an acyl group, provided that when $R^1$ is (1) a $C_{1-4}$ alkanoyl group, (2) benzoyl, (3) trifluoroacetyl, (4) sulfamoyl which may optionally be substituted with a $C_{1-4}$ alkyl group, (5) a $C_{1-4}$ alkyl group which may optionally be substituted with hydroxy, halogen or a $C_{1-3}$ alkoxy group, (6) amino which is substituted with a $C_{14}$ alkyl group, A is $-CH=$, $R^2$ is a hydrogen atom, $X^1$ is a chlorine atom, $R^3$ is a chlorine atom, and $X^2$ is a hydrogen atom, then $R^4$ is an optionally substituted alkyl group or an optionally substituted acyl group; or salts thereof, their production and use thereof. These compounds and salts thereof are useful as antiprotozoal agents.

18 Claims, No Drawings

1,2,4-TRIAZINE-3, 5-DIONE DERIVATIVES, THEIR PRODUCTION AND USE THEREOF

FIELD OF THE INVENTION

The present invention relates to a novel triazine derivative, or a salt thereof, and use thereof. Particularly, the invention relates to a novel triazine derivative or a salt thereof and to an anti-protozoal composition which is useful for control of parasitic protozoa such as coccidia.

BACKGROUND OF THE INVENTION

Parasitic protozoa are ubiquitous in animals such as mammals, fowls, fish, and insects. Parasitizing their internal organs, skin, and eyes in most instances, these organisms inflict serious damages on the hosts, thus playing a great economic havoc with the animal, poultry, and fish industries. Coccidiosis, which is a protozoal disease in domestic fowls, is mostly caused by several species of protozoa belonging to the genus Eimeria, such as *E. tenella, E. necatrix, E. acervulina, E. maxima, E. brunetti*, and *E. mivati*. For example, *E. tenella*, parasitizes the intestinal canal wall, such as the cecal wall, of poultry to do fatal harm to the host. Thus, this infectious disease manifests itself in the form of erosion, inflammation and hemorrhage of the intestinal wall and blood retention in the cecum due to extensive invasion into the bowels, with the accompanying symptoms such as poor appetite and retarded growth. Internal parasitic protozoa are usually transmitted orally. However, in the case of coccidiosis, the oocysts of the parasites cannot be effectively inactivated even by the intensive disinfection with potassium dichromate solution and, moreover, their life span is as short as about 7 days. Therefore, one has to just sit and see the hazard speading.

In the case of fish, protozoa parasitizing their external organs are serious problems of concern. Their parasitization results in injuries of the skin and gills, weakens the resistance of the host to infections and even may directly cause death. In the culture of fish on a large-scale pisciculture farm, parasitic protozoa spread rapidly throughout the whole pond of fish and the consequent economic loss cannot be tolerated.

The same is true of insects. Taking bees as an example, protozoa represented by *Nosema apis* are playing havocs with apiculturists all over the world. The above protozoa destroy the internal organs of bees to compromise their resistance, thus making the hosts prone to other diseases.

A large number of chemicals are known for the control of parasitic protozoa but most of those chemicals are host-specific or of narrow spectrum and with some of the chemicals, the emergence of resistant protozoa has been reported. Furthermore, because of their weak activity, those chemicals have to be administered in massive doses, thus being not fully satisfactory from economic and ecological points of view. Therefore, development of a chemical substance that can be used for control of parasitic protozoa in vertebrate animals such as mammals, fowls, fish, and insects with a sufficiently broad spectrum as well as potent activity has been demanded.

As such a chemical, a 2-phenyl-6-azauracil derivative was found to have anticoccidial activity (J. Med. Chem., 22, 1483, 1979) and, accordingly, a variety of 6-azauracil derivatives were synthesized and evaluated. However, those compounds were found to be teratogenic and no further development was made. Then, as compounds overcoming the teratogenicity problem, 2-phenyl-1,2,4-triazinedione compounds such as a 2-( 4-phenoxyphenyl)-1,2,4-triazine derivative [DE-A-2532363], a 2-[4-(1-cyano-1-phenylmethyl)phenyl]-1,2,4-triazine derivative, etc. were developed and some of them are already in field use as anticoccidial agents in the Europe and other countries including Australia, although they have not been approved for use as yet in the rest of the world including Japan and the United States.

SUMMARY OF THE INVENTION

Starting from the above state of the art the inventors of the present invention proceeded with research and found that a series of novel triazine derivatives has potent activity against parasitic protozoa. Further intensive research has revealed that this series of derivatives are suitable for controlling the various parasitic protozoa encountered in routine breeding (vertebrates such as mammalian animals, fowls, and fish; insects, etc.) with low toxicity, a low residual activity, and high biological efficacy even against strains resistant to the conventional chemicals, thus assuring safety. The present invention is based on the above findings.

The present invention relates to a compound represented by the formula:

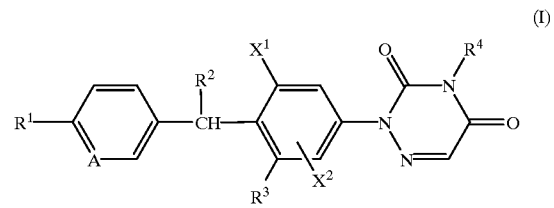

wherein $R^1$ is (1) an optionally substituted alkyl group which may be bonded through a hetero atom, (2) an optionally substituted acyl group, (3) an alkylsulfonyl group, (4) an alkylsulfinyl group, or (5) an optionally substituted sulfamoyl group;

A is —N= or —CH=;

$R_2$ is a hydrogen atom or an alkyl group which may optionally be substituted with halogen and which may be bonded through a hetero atom;

$X^1$ is halogen or a lower alkyl group;

$X^2$ is a hydrogen atom or a fluorine atom;

$R^3$ is a hydrogen atom, halogen or a lower alkyl group; and $R^4$ is a hydrogen atom, an optionally substituted alkyl group or an acyl group; or a salt thereof, its production and use thereof.

Specifically, the present invention relates to:

[1] a compound represented by the formula:

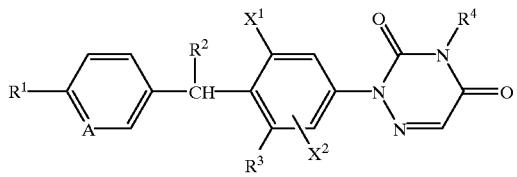

wherein $R^1$ is (1) an optionally substituted alkyl group which may be bonded through a hetero atom, (2) an optionally substituted acyl group, (3) an alkylsulfonyl group, (4) an alkylsulfinyl group, or (5) an optionally substituted sulfamoyl group;

A is —N= or —CH=; $R^2$ is a hydrogen atom or an alkyl group which may optionally be substituted with halogen and which may be bonded through a hetero atom;

3

$X^1$ is halogen or a lower alkyl group;

$X^2$ is a hydrogen atom or a fluorine atom;

$R^3$ is a hydrogen atom, halogen or a lower alkyl group; and $R^4$ is a hydrogen atom, an optionally substituted alkyl group or an optionally substituted acyl group, provided that when $R^1$ is (1) a $C_{1-4}$ alkanoyl group, (2) benzoyl, (3) trifluoroacetyl, (4) sulfamoyl which may optionally be substituted with $C_{1-4}$ alkyl, (5) a $C_{1-4}$ alkyl group which may optionally be substituted with hydroxy, halogen or $C_{1-3}$ alkoxy, (6) an amino group which is substituted with $C_{1-4}$ alkyl, A is —CH═, $R^2$ is a hydrogen atom, $X^1$ is a chlorine atom, $R^3$ is a chlorine atom, and $X^2$ is a hydrogen atom, then $R^4$ is an optionally substituted alkyl group or an optionally substituted acyl group; or a salt thereof, [2] the compound as described in [1] above, which is represented by the formula:

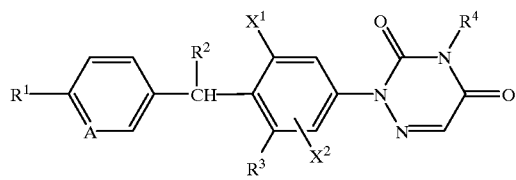

wherein $R^1$ is (1) an alkyl group which is substituted with (i) aryl, (ii) alkylidene, (iii) mercapto which may optionally be substituted, (iv) imino which may optionally be substituted or (v) amino which may optionally be substituted, or (2) a group of the formula: $R^8$—S(O)n— wherein $R^8$ is an alkyl group and n is 1 or 2; A is —N═ or —CH═; $R^2$ is a hydrogen atom or an alkyl group which may optionally be substituted with halogen and which may be bonded through a hetero atom;

$X^1$ is a halogen atom or a lower alkyl group; $X^2$ is a hydrogen atom or a fluorine atom; $R^3$ is a hydrogen atom, a halogen atom or a lower alkyl group; and $R^4$ is a hydrogen atom, an optionally substituted alkyl group or an optionally substituted acyl group; or a salt thereof,

[3] the compound as described in [2] above, wherein $R^1$ is (1) a $C_{1-7}$ alkyl group which is substituted with (i) $C_{6-14}$ aryl, (ii) $C_{1-3}$ alkylidene, (iii) mercapto which may optionally be substituted with a $C_{1-3}$ alkyl group, (iv) imino which may optionally be substituted with a hydroxy group or a $C_{1-4}$ alkoxy group, or (v) phenylsulfonylamino which may optionally be substituted with $C_{1-3}$ alkyl, (2) a $C_{1-4}$ alkylthio group, (3) a $C_{1-4}$ alkylsulfonyl group, or (4) a $C_{1-4}$ alkylsulfinyl group;

A is —N═ or —CH═; $R^2$ is a hydrogen group; $X^1$ is a halogen atom; $X^2$ is a hydrogen atom; $R^3$ is a halogen atom; and $R^4$ is a hydrogen atom; or a salt thereof,

[4] the compound as described in [2] above, which is 2-{3,5-dichloro-4-[4-(propen-2-yl)benzyl]phenyl}-1,2,4-triazine-3,5(2H,4H)-dione or 2-{3,5-dichloro-4-[4-(1-tosylaminoethyl)benzyl]phenyl}-1,2,4-triazine-3,5(2H,4H)-dione; or a salt thereof,

[5] the compound as described in [1] above, which is represented by the formula:

4

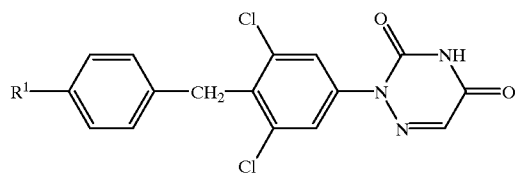

wherein $R^1$ is (1) a benzoyl group which is substituted with halogen, (2) a halogenated alkyl group which may optionally be substituted with hydroxy, (3) an alkanoyl group which is substituted with halogen or (4) an alkoxy group; or a salt thereof,

[6] the compound as described in [5] above, wherein $R^1$ is (1) a benzoyl group which is substituted with halogen, (2) a halogenated $C_{1-4}$ alkyl group which may optionally be substituted with hydroxy, (3) a $C_{1-4}$ alkanoyl group which is substituted with halogen, or (4) a $C_{1-4}$ alkoxy group; or a salt thereof,

[7] the compound as described in [5] above, which is 2-{3,5-dichloro-4-[4-(1-fluoro-1-methylethyl)benzyl]phenyl}-1,2,4-triazine-3,5(2H,4H)-dione or 2-{4-[4-(α-chloromethyl-α-hydroxyethyl)benzyl]-3,5-dichlorophenyl}-1,2,4-triazine-3,5(2H,4H)-dione; or a salt thereof,

[8] the compound as described in [1] above, which is represented by the formula:

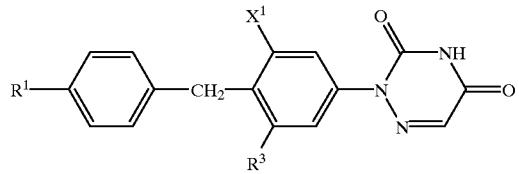

wherein $R^1$ is (1) an alkyl group which may optionally be substituted with hydroxy or (2) an alkanoyl group;

$X^1$ is a lower alkyl group or a bromine atom; and $R^3$ is a lower alkyl group or a halogen atom; or a salt thereof,

[9] the compound as described in [8] above, wherein $R^1$ is (1) a $C_{1-4}$ alkyl group which may optionally be substituted with hydroxy or (2) a $C_{1-4}$ alkanoyl group; or a salt thereof,

[10] the compound as described in [8] above, wherein $R^1$ is a $C_{1-4}$ alkyl group which is substituted with hydroxy, or a salt thereof,

[11] the compound as described in [8] above, which is 2-{3-bromo-5-chloro-4-[4-(1-hydroxy-1-methylethyl)benzyl ]phenyl}-1,2,4-triazine-3,5(2H,4H)-dione, 2-{3-chloro-4-[4-(1-hydroxy-1-methylethyl)benzyl]-3-methylphenyl}-1,2,4-triazine-3,5(2H,4H)-dione, 2-{3,5-dibromo-4-[4-(1-hydroxy-1-methylethyl)benzyl]phenyl}-1,2,4-triazine-3,5(2H,4H)-dione or 2-{3,5-dibromo-4-[4-(1-hydroxyethyl)benzyl]phenyl}-1,2,4-triazine-3,5(2H,4H)-dione; or a salt thereof,

[12] the compound as described in [1] above, which is represented by the formula:

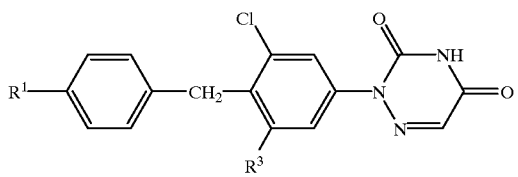

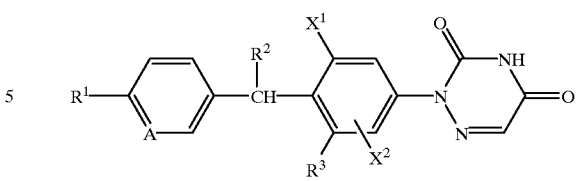

wherein $R^1$ is a $C_{1-4}$ alkanoyl group, and $R^3$ is a lower alkyl group; or a salt thereof.

[13] the compound as described in [12] above, which is 2-[4-(4-acetylbenzyl)-3-chloro-5-methylphenyl]-1,2,4-triazine-3,5(2H,4H)-dione or a salt thereof,

[14] 2-{3,5-dichloro-4-[4-(1-hydroxy-1-methylethyl)benzyl]phenyl}1-1,2,4-triazine-3,5(2H,4H)-dione or a salt thereof,

[15] an anti-protozoal composition comprising an effective amount of the compound as described in [1] or [14] above or a salt thereof, and a pharmaceutical acceptable carrier, excipient or diluent,

[16] a method for producing of the compound as described in [1] above, which comprises:

(a) subjecting a compound of the formula:

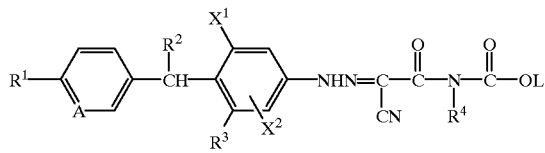

wherein L is a hydrogen atom, a $C_{1-3}$ alkyl group or an aryl group, and the other symbols have the same meaning as defined in [1] above, or a salt thereof to a cyclization reaction, a hydrolysis reaction of cyano, and a decarboxylation reaction to provide a compound of the formula:

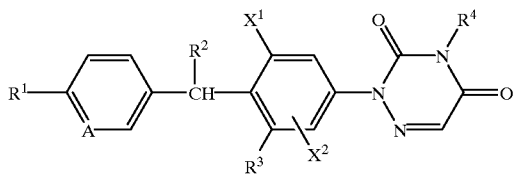

wherein each symbol has the same meaning as defined in [1] above; or a salt thereof, (b) subjecting a compound of the formula:

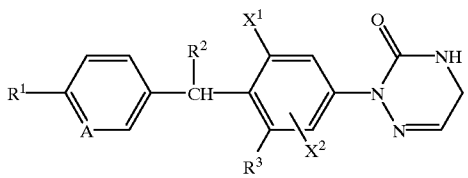

wherein each symbol has the same meaning as defined in [1] above; or a salt thereof to an oxidation reaction to provide a compound of the formula:

wherein each symbol has the same meaning as defined in [1] above; or a salt thereof, and if necessary, (c) reacting the resulting compound as described in [1] above wherein $R^4$ is a hydrogen atom, or a salt thereof with an acylating agent or an alkylating agent to provide the compound as claimed in claim 1 wherein $R^4$ is an optionally substituted alkyl group or an optionally substituted acyl group, or a salt thereof,

[17] use of the compound as described in [1] or [14] above, for the manufacture of an anti-protozoal composition, and

[18] a method for preventing or treating sporozoasis in a vertebrate or an insect which comprises administering an effective amount of the antiprotozoal composition as described in [15] above, to the vertebrate or insect.

Referring to formula (I), the alkyl group of the optionally substituted alkyl group which may be bonded through a hetero atom as mentioned for $R^1$ includes a $C_{1-7}$ alkyl group such as straight-chain or branched $C_{1-4}$ alkyl group, e.g. methyl, ethyl, propyl, isopropyl, butyl, isobutyl, sec-butyl, tert-butyl, etc. and $C_{3-7}$ cycloalkyl, e.g. cyclopropyl, cyclohexyl, etc.

The substituent which may be present on said alkyl includes (1) a $C_{1-3}$ alkylidene group such as methylene ($CH_2=$), ethylidene, propylidene, or isopropylidene; (2) a $C_{1-3}$ alkylidyne group such as methylidyne, ethylidyne, or propylidyne; (3) an optionally substituted $C_{6-14}$ aryl group (e.g. phenyl, 1-naphthyl, 2-naphthyl, etc.); (4) a $C_{1-3}$ alkoxy group such as methoxy, ethoxy, propoxy, or isopropoxy; (5) an optionally substituted $C_{6-14}$ aryloxy group (e.g. phenoxy, etc.); (6) a di-$C_{1-3}$ alkylamino group such as dimethylamino, diethylamino, dipropylamino, or diisopropylamino; (7) a $C_{1-3}$ alkylamino group such as methylamino, ethylamino, propylamino or isopropylamino; (8) phenylsulfonylamino which may optionally be substituted with 1 to 3 $C_{1-3}$ alkyl groups such as methyl, ethyl and propyl; (9) nitro; (10) cyano; (11) a mercapto group which may optionally be substituted with a $C_{1-3}$ alkyl group such as methyl, ethyl, propyl or isopropyl; (12) an imino group which may optionally be substituted with (i) a $C_{1-4}$ alkoxy group such as methoxy, ethoxy or propoxy, or (ii) hydroxy; (13) a halogen atom such as fluorine or chlorine; and (14) hydroxy.

The number of the substituents is preferably 1 to 3.

The substituent which may be present on said $C_{6-11}$, aryl group or $C_{6-14}$ aryl group of $C_{6-14}$ aryloxy group includes (1) a halogen atom such as fluorine, chlorine or bromine; (2) a $C_{1-4}$ alkyl group such as methyl, ethyl, propyl or isopropyl in which the alkyl may optionally be substituted with 1 to 3 substituents selected from the group consisting of (i) halogen such as fluorine, chlorine or bromine and (ii) hydroxy; (3) a $C_{1-4}$ alkoxy group such as methoxy, ethoxy or propoxy; (4) a $C_{1-4}$ alkyl-carbonyl group such as formyl, acetyl or propionyl; (5) a $C_{1-4}$ alkylthio group such as methylthio, ethylthio or propylthio; (6) hydroxy; (7) nitro; and (8) cyano.

The number of the substituents is preferably 1 to 3.

The hetero atom mentioned above includes a sulfur atom, an oxygen atom, and a nitrogen atom.

Here, an alkyl group bonded through a nitrogen atom includes a mono- or di-alkyamino group.

An alkyl group bonded through an oxygen atom includes an alkoxy group. An alkyl group bonded through a sulfur atom includes an alkylsulfinyl group and an alkylsulfonyl group as mentioned hereinafter besides an alkylthio group.

Such an optionally substituted alkyl group which may be bonded through a hetero atom preferably includes an α-hydroxy substituted $C_{1-4}$ alkyl group (e.g. hydroxymethyl, 1-hydroxyethyl, 1-hydroxypropyl, 1-hydroxy-1-methylethyl, etc.), a $C_{1-4}$ alkyl group which is substituted with 1 to 3 halogens (e.g. fluoromethyl, 1- or 2-fluoroethyl, 1- or 2-chloroethyl, 1-, 2- or 3-fluoropropyl, 1-fluoro-1-methylethyl, difluoromethyl, trifluoromethyl, 1,1-difluoroethyl, etc.), an α-hydroxy-$C_{1-4}$ alkyl group which is substituted with 1 to 3 halogens (e.g. 1-hydroxy-1-methyl-2-chloroethyl etc.), a $C_{1-4}$ alkyl group which is substituted with imino which is substituted with hydroxy or a $C_{1-4}$ alkoxy group (e.g. 1-hydroxyiminoethyl, 1-methoxyiminoethyl, etc.), a $C_{1-4}$ alkyl group which is substituted with methylene ($CH_2=$) (e.g. vinyl, allyl, 2-methylallyl, isopropenyl, 3-butenyl, etc.), a mercapto group which is substituted with a $C_{1-4}$ alkyl group (e.g. methylthio, ethylthio, etc.), a $C_{1-4}$ alkyl group which is substituted with a $C_{6-14}$ arylsulfonylamino group which may optionally be substituted with a $C_{1-4}$ alkyl group (e.g. 1-tosylaminoethyl, etc.), a $C_{6-14}$ aryl-$C_{1-4}$ alkyl group (e.g. benzyl, etc.), a $C_{1-4}$ alkoxy group (e.g. methoxy, ethoxy, propoxy, isopropoxy, etc.).

The acyl group of the optionally substituted acyl group as mentioned for $R^1$ includes a $C_{1-15}$ acyl group (preferably $C_{1-8}$ acyl group) such as, for example, a $C_{1-4}$ alkanoyl group such as formyl, acetyl, propionyl, butyryl or isobutyryl; a $C_{3-7}$ cycloalkyl-carbonyl group such as cyclopropylcarbonyl or cyclohexylcarbonyl; a $C_{6-14}$ aryl-carbonyl group such as benzoyl or naphthylcarbonyl; and a $C_{7-12}$ aralkyl-carbonyl group such as phenyl-$C_{1-4}$ alkyl carbonyl (e.g. benzylcarbonyl, phenethylcarbonyl, etc.) or naphthyl-$C_{1-2}$ alkylcarbonyl (e.g. naphthylmethylcarbonyl).

The substituent which may be present on said acyl group includes a $C_{1-4}$ alkyl group such as methyl, ethyl, propyl, isopropyl, or tert-butyl, a $C_{2-4}$ alkenyl group such as vinyl, 1-methylvinyl, 1-propenyl, or allyl, a $C_{2-4}$ alkynyl group such as ethynyl, 1-propynyl, or propargyl, a $C_{6-14}$ aryl group such as phenyl, a $C_{1-3}$ alkoxy group such as methoxy, ethoxy, propoxy, or isopropoxy, phenoxy, a di-$C_{1-3}$ alkylamino group such as dimethylamino, diethylamino, dipropylamino, or diisopropylamino, a $C_{1-3}$ alkylamino group such as methylamino, ethylamino, propylamino, or isopropylamino, nitro, cyano, $C_{1-3}$ alkylthio such as methylthio, ethylthio, propylthio, or isopropylthio, halogen such as fluorine, chlorine, or bromine, and hydroxy. Especially preferred is a halogen atom among substituents as mentioned above. The number of substituents is preferably 1 to 3.

Such an optionally substituted acyl group preferably includes a $C_{1-4}$ alkanoyl group which may optionally be substituted with 1 to 3 halogens (e.g. methylcarbonyl, ethylcarbonyl, chloromethylcarbonyl, etc.) and a benzoyl group which may optionally be substituted with 1 to 3 halogens (e.g. 4-chlorobenzoyl, etc.).

The alkyl group of the alkylsulfonyl group or the alkylsulfinyl group as mentioned for $R^1$ includes a $C_{1-4}$ alkyl group such as methyl, ethyl, propyl, or isopropyl.

The substituent which may be present on said sulfamoyl group as to the optionally substituted sulfamoyl group includes a $C_{1-4}$ alkyl group such as methyl, ethyl, propyl, or isopropyl.

The number of substituents is 1 or 2.

The alkyl group of the optionally substituted alkyl group which may be bonded through a hetero atom 2 as mentioned for $R^2$ includes a $C_{1-3}$ alkyl group such as methyl, ethyl, propyl, or isopropyl, and a $C_{1-3}$ alkyl group which is substituted with 1 to 3 halogens such as chloromethyl, dichloromethyl, trichloromethyl, trifluoromethyl, or trifluoroethyl. The hetero atom may be an oxygen atom, a sulfur atom or a nitrogen atom, and the alkyl bonded through such a hetero atom includes a $C_{1-3}$ alkoxy group such as methoxy, ethoxy, propoxy, or isopropoxy; a $C_{1-3}$ alkylthio group such as methylthio, ethylthio, propylthio, or isopropylthio; and a mono- or di-($C_{1-3}$ alkyl) amino group such as methylamino, ethylamino, propylamino, dimethylamino, or diethylamino.

$R^2$ is preferably hydrogen or methyl.

The halogen as mentioned for $X^1$ includes fluorine, chlorine, bromine, or iodine. Preferred is chlorine or bromine. The lower alkyl group as mentioned for $X^1$ includes a $C_{1-3}$ alkyl group such as methyl, ethyl, propyl or isopropyl. Especially preferred among them is methyl.

Between hydrogen and fluorine for $X^2$, hydrogen is preferred.

$R^3$ includes a hydrogen atom, a halogen atom, or a lower alkyl group. The halogen atom includes fluorine, chlorine, bromine, or iodine, and chlorine or bromine being preferred. The lower alkyl group includes a $C_{1-3}$ alkyl group such as methyl, ethyl, or isopropyl, and methyl being preferred.

The alkyl group of the optionally substituted alkyl as mentioned for $R^4$ includes a $C_{1-3}$ alkyl group such as methyl, ethyl, or isopropyl. The acyl for $R^4$ includes a $C_{1-7}$ acyl group such as a $C_{1-4}$ alkanoyl (e.g. formyl, acetyl, propionyl, etc.), or benzoyl.

Each of the above-mentioned alkyl group and acyl group may have a substituent or substituents selected from a group consisting of a $C_{2-4}$ alkenyl group such as vinyl, 1-methylvinyl, 1-propenyl, or allyl; a $C_{2-4}$ alkynyl group such as ethynyl, 1-propynyl, or propargyl; a $C_{6-14}$ aryl group such as phenyl; a $C_{1-3}$ alkoxy group such as methoxy, ethoxy, propoxy, or isopropoxy; a $C_{6-14}$ aryloxy group such as phenoxy; a di-$C_{1-3}$ alkylamino group such as dimethylamino, diethylamino, dipropylamino, or diisopropylamino; a $C_{1-3}$ alkylamino group such as methylamino, ethylamino, propylamino, or isopropylamino; nitro; cyano; a $C_{1-3}$ alkylthio group such as methylthio, ethylthio, propylthio, or isopropylthio; halogen such as fluorine, or chlorine; and hydroxy. The number of substituents is 1 to 3. Especially preferred $R^4$ is a hydrogen atom.

With regard to the formula (I), when $R^1$ is (1) a $C_{1-4}$ alkanoyl group (e.g. formyl, acetyl, propionyl, butyryl, etc.), (2) benzoyl, (3) trifluoroacetyl, (4) sulfamoyl which may optionally be substituted with $C_{1-3}$ alkyl (e.g. methylamino sulfonyl, dimethylaminosulfonyl, etc.), (5) a $C_{1-4}$ alkyl group which may optionally be substituted with (i) hydroxy, (ii) halogen (e.g. fluorine, chlorine, bromine, iodine) or (iii) $C_{1-3}$ alkoxy (e.g. methoxy, ethoxy, etc.), (6) amino which is substituted with $C_{1-4}$ alkyl (e.g. dimethylamino, diethylamino, etc.); A is —CH=; $R^2$ is a hydrogen atom; $X^1$ is a chlorine atom; $R^3$ is a chlorine atom; and $X^2$ is a hydrogen atom, then $R^4$ is preferably an optionally substituted alkyl group or an optionally substituted acyl group.

Among the compounds represented by the formula (I), compounds represented by following (a), (b), (c), (d) or (e) or salt thereof are preferable.

(a) A compound represented by the formula:

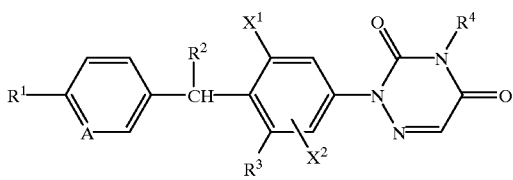

wherein $R^1$ represents a group of (1) or (2) as mentioned below.

(1) an alkyl group which may optionally be substituted with (i) aryl, (ii) alkylidene, (iii) mercapto which may optionally be substituted, (iv) imino which may optionally be substituted, or (v) amino which may optionally be substituted.

The aryl group as mentioned above includes a $C_{6-14}$ aryl group such as phenyl, 1-naphthyl or 2-naphthyl.

The alkylidene group as mentioned above includes a $C_{1-3}$ alkylidene group such as methylene ($CH_2=$), ethylidene, propylidene or isopropylidene.

The substituent of mercapto as mentioned above includes a $C_{1-4}$ alkyl group such as methyl, ethyl, propyl, or isopropyl.

The substituent of imino as mentioned above includes hydroxy and a $C_{1-4}$ alkoxy group such as methoxy, ethoxy, propoxy or isopropoxy.

The substituent of amino as mentioned above includes phenylsulfonyl which may optionally be substituted with 1 to 3 $C_{1-3}$ alkyl groups such as methyl, ethyl, propyl, and isopropyl. The number of the substituent for amino is preferably one.

(2) a group of the formula $R^8$—S(O)n— wherein $R^8$ is an alkyl group and n is 1 or 2.

In the above formula, the alkyl group as mentioned for $R^8$ includes a straight-chain or branched $C_{1-4}$ alkyl group such as methyl, ethyl, propyl, isopropyl, butyl, isobutyl, sec-butyl or tert-butyl. Specific examples of the group of the formula $R^8$—S(O)n— include a $C_{1-4}$ alkylsulfonyl group, and a $C_{1-4}$ alkylsulfinyl group.

In the formula as mentioned above, A represents —N= or —CH=.

$R^2$ represents a hydrogen atom or an alkyl group which may optionally be substituted with halogen (e.g. fluorine, chlorine, bromine, iodine) and which may be bonded through a hetero atom (e.g. oxygen, sulfur, nitrogen).

The alkyl group includes a $C_{1-3}$ alkyl group such as methyl, ethyl, propyl or isopropyl.

Especially preferably $R^2$ is a hydrogen atom.

In the above formula, $X^1$ is halogen (e.g. fluorine, chlorine, bromine, iodine) or a lower alkyl group (e.g. a $C_{1-3}$ alkyl group such as methyl, ethyl, propyl or isopropyl). As $X^1$, halogen is preferable.

$X^2$ represents a hydrogen atom or a fluorine atom. Among them, a hydrogen atom is preferable.

$R^3$ represents a hydrogen atom, a halogen atom (e.g. fluorine, chlorine, bromine, iodine) or a lower alkyl group (e.g. a $C_{1-3}$ alkyl group such as methyl, ethyl, propyl or isopropyl). Among them, halogen is especially preferable.

$R^4$ represents a hydrogen atom, an optionally substituted alkyl group or an optionally substituted acyl group.

The alkyl group of the optionally substituted alkyl group as mentioned for $R^4$ includes a $C_{1-3}$ alkyl group such as methyl, ethyl, or isopropyl. Also, the acyl group includes a $C_{1-7}$ acyl group such as a $C_{1-4}$ alkanoyl group, e.g. formyl, acetyl, or propionyl; or benzoyl.

Such an alkyl group or an acyl group may have substituents selected from the group consisting of (1) a $C_{2-4}$ alkenyl group such as vinyl, 1-methylvinyl, 1-propenyl, and allyl; (2) a $C_{2-4}$ alkynyl group such as ethynyl, 1-propynyl, or propargyl; (3) a $C_{6-14}$ aryl group such as phenyl; (4) a $C_{1-3}$ alkoxy group such as methoxy, ethoxy, propoxy, or isopropoxy; (5) a $C_{6-14}$ aryloxy group such as phenoxy; (6) di-$C_{1-3}$ alkylamino group such as dimethylamino, diethylamino, dipropylamino, or diisopropylamino; (7) a $C_{1-3}$ alkylamino group such as methylamino, ethylamino, propylamino, or isopropylamino; (8) nitro; (9) cyano; (10) a $C_{1-3}$ alkylthio group such as methylthio, ethylthio, propylthio, or isopropylthio; (11) halogen such as fluorine or chlorine; and (12) hydroxy.

The number of substituents is preferably 1 to 3.

$R^4$ is preferably a hydrogen atom.

Such a compound is specifically includes 2-{3,5-dichloro-4-[4-(propen-2-yl)benzyl]phenyl}-1,2,4-triazine-3,5(2H,4H)-dione:

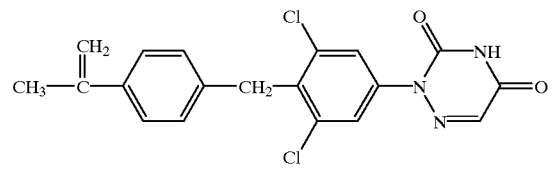

and 2-{3,5-dichloro-4-[4-(1-tosylaminoethyl)benzyl]phenyl}-1,2,4-triazine-3,5(2H,4H)-dione:

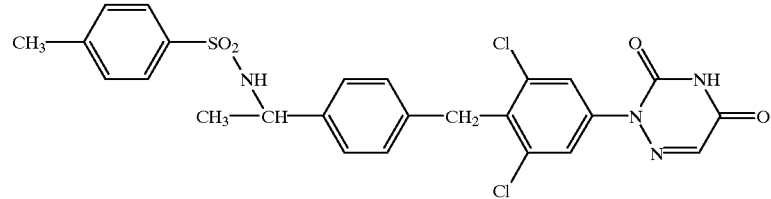

(b) A compound represented by the formula:

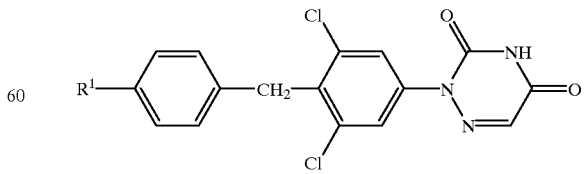

wherein $R^1$ represents a group of (1) to (4) as mentioned below.

(1) a benzoyl group which is substituted with 1 to 3 halogens (e.g. fluorine, chlorine, bromine, iodine);
(2) a halogenated alkyl group which may optionally be substituted with 1 to 3 hydroxy groups at substitutable positions. The number of halogens on the alkyl group is 1 to 3;
(3) an alkanoyl group which is substituted with 1 to 3 halogens (e.g. fluorine, chlorine, bromine, iodine).

The alkanoyl group includes a straight-chain or branched $C_{1-4}$ alkanoyl group such as methylcarbonyl, ethylcarbonyl, propylcarbonyl, isopropylcarbonyl, butylcarbonyl, isobutylcarbonyl, sec-butylcarbonyl, or tert-butylcarbonyl;

(4) an alkoxy group (e.g. a $C_{1-4}$ alkoxy group such as methoxy, ethoxy, propoxy, or isopropoxy);

Such a compound is specifically includes 2-{3,5-dichloro-4-[4-(1-fluoro-1-methylethyl)benzyl]phenyl}-1,2,4-triazine-3,5(2H,4H)-dione:

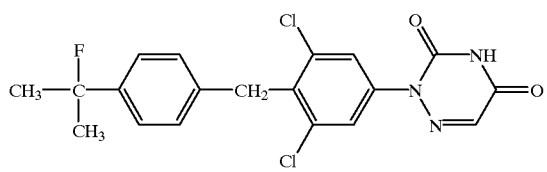

and 2-{4-[4-(α-chloromethyl-α-hydroxyethyl)benzyl]-3,5-dichlorophenyl}-1,2,4-triazine-3,5(2H,4H)-dione:

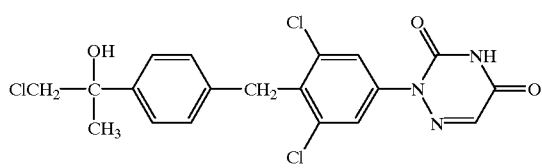

(c) A compound represented by the formula:

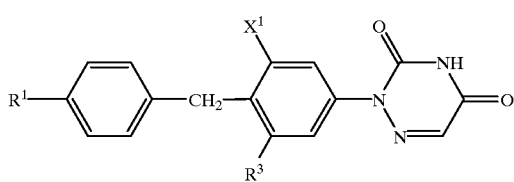

wherein $R^1$ represents an alkyl group which may optionally be substituted with hydroxy or an alkanoyl group.

The alkyl group includes a straight-chain or branched $C_{1-4}$ alkyl group such as methyl, ethyl, propyl, isopropyl, butyl, isobutyl, sec-butyl, or tert-butyl. Among them, ethyl and isopropyl are preferable.

The hydroxy group which may be present on the alkyl group is preferably substituted at the α-position on the alkyl group.

The above alkanoyl group includes a $C_{1-4}$ alkanoyl group such as methycarbonyl, ethylcarbonyl, propylcarbonyl or isopropylcarbonyl. Among them, methylcarbonyl (acetyl) is especially preferable.

In the above formula, $X^1$ represents a lower alkyl group or a bromine atom.

The lower alkyl group includes a $C_{1-3}$ alkyl group such as methyl, ethyl, propyl, or isopropyl, and preferred being methyl.

$R^3$ represents a lower alkyl group or halogen.

The lower alkyl group for $R^3$ has the same meaning as defined in lower alkyl group for $X^1$. Especially, methyl is preferable.

Such a compound is specifically includes 2-{3-bromo-5-chloro-4-[4-(1-hydroxy-1-methylethyl)benzyl]phenyl}-1,2,4-triazine-3,5(2H,4H)-dione:

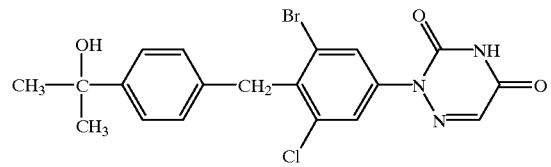

2-{3-chloro-4-[4-(1-hydroxy-1-methylethyl)benzyl]-5-methylphenyl}-1,2,4-triazine-3,5(2H,4H)-dione:

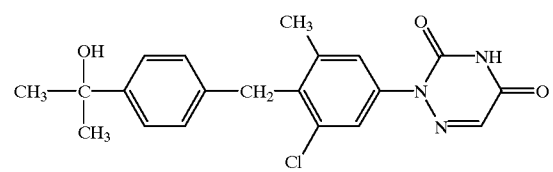

2-{3,5-dibromo-4-[4-(1-hydroxy-1-methylethyl)benzyl]phenyl}-1,2,4-triazine-3,5(2H,4H)-dione:

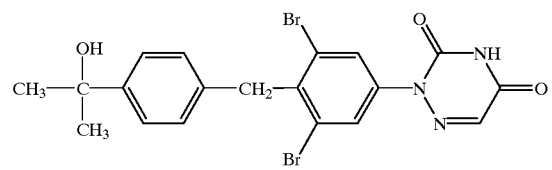

and 2-{3,5-dibromo-4-[4-(1-hydroxyethyl)benzyl]phenyl}-1,2,4-triazine-3,5(2H,4H)-dione:

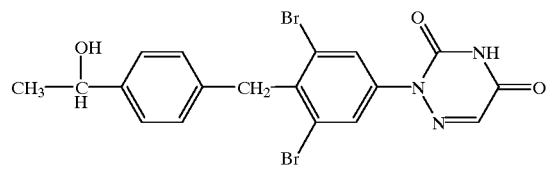

(d) A compound represented by the formula:

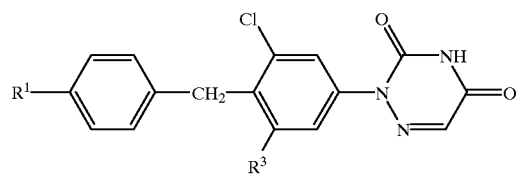

wherein $R^1$ represents a $C_{1-4}$ alkanoyl group, and R represents a lower alkyl group.

The $C_{1-4}$ alkanoyl group for $R^1$ includes methylcarbonyl or ethylcarbonyl, and preferred being methylcarbonyl (acetyl).

The lower alkyl group for $R^3$ includes a $C_{1-3}$ alkyl group such as methyl, ethyl, propyl, or isopropyl. Among them, methyl is preferable.

Such a compound is specifically includes 2-[4-(4-acetylbenzyl)-3-chloro-5-methylphenyl]-1,2,4-triazine-3,5(2H,4H)-dione:

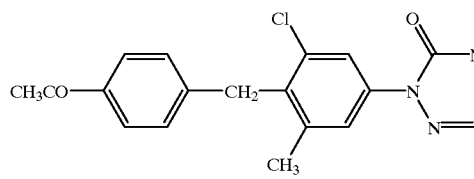
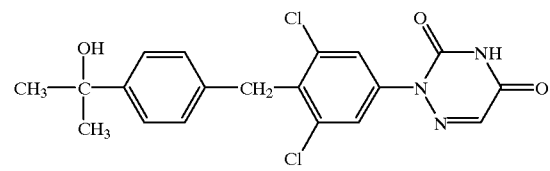
(e) A compound which is 2-{3,5-dichloro-4-[4-(1-hydroxy-1-methylethyl)benzyl]phenyl}-1,2,4-triazine-3,5(2H,4H)-dione:
The triazine derivative (I) of the present invention (hereinafter referred to briefly as the compound (I)) can be produced by, for example, the following processes.
Process a)
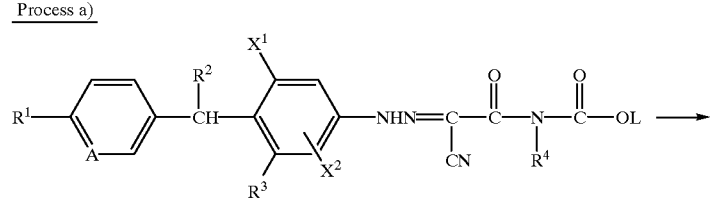
(IVa)
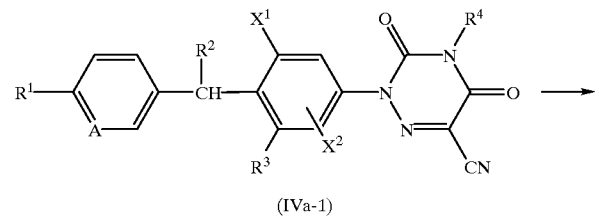
(IVa-1)
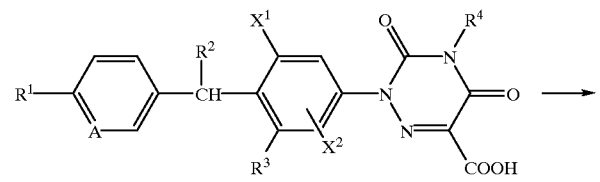
(IVa-2)
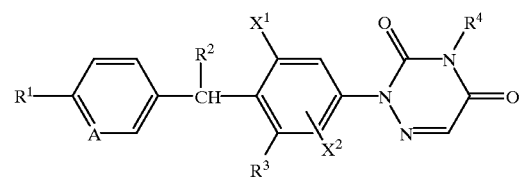
(I)
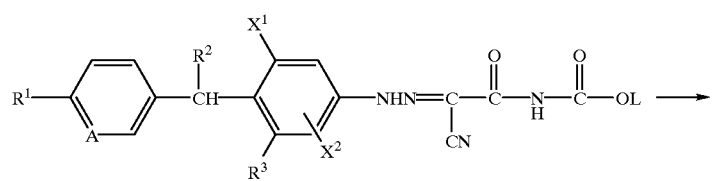
(IVb)
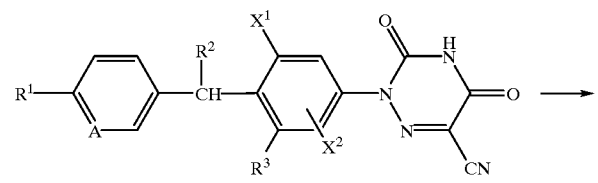
(IVb-1)

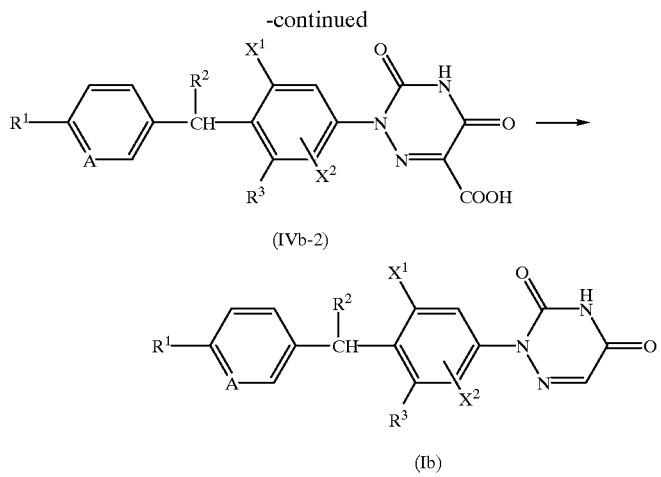

(IVb-2)

(Ib)

wherein $R^1$, A, $X^1$, $X^2$, $R^2$, $R^3$, and $R^4$ are as defined hereinbefore; L represents hydrogen, a $C_{1-3}$ alkyl group (e.g. methyl, ethyl, propyl, isopropyl, etc.), or a $C_{6-14}$ aryl group (e.g. phenyl, etc.).

In this process a), a hydrazone derivative (IVa) or (IVb) is cyclized and, after hydrolysis of the cyano group, the cyclized compound is subjected to a decarboxylation reaction to provide compound (I) or (Ib).

The cyclization reaction of compound (IVa) or (IVb) is generally conducted under heating in an inert solvent or in the absence of a solvent, optionally in the presence of a Lewis acid or a Lewis base in accordance with the procedure described in Monatshefte der Chemie, 94, 258–262, 1963. The reaction temperature is generally about 60 to about 200° C. and preferably about 100 to about 160° C. For this reaction, virtually any inert organic solvent can be employed. Thus, it may be any of the reaction solvents which are generally used in organic chemistry, for example, aliphatic or aromatic hydrocarbons (e.g. benzene, ligroin, benzine, toluene, xylene, etc.), halogenated hydrocarbons (e.g. ethylene chloride, chloroform, carbon tetrachloride, dichloroethane, chlorobenzene, o-dichlorobenzene, etc.), ethers (e.g. dibutyl ether, glycol dimethyl ether, diglycol dimethyl ether, tetrahydrofuran, dioxane, etc.), ketones (e.g. methyl ethyl ketone, methyl isopropyl ketone, methyl isobutyl ketone, etc.), esters (e.g. ethyl acetate etc.), nitriles (e.g. acetonitrile, propionitrile, etc.), amides (e.g. dimethylformamide, dimethylacetamide, hexamethylphosphorotriamide, etc.), N-methylpyrrolidone, dimethylsulfoxide, tetramethylenesulfone, mercaptoacetic acid, pyridine, and so on. This reaction may be carried out while the byproduct such as alcohol is removed.

The hydrolysis reaction of the cyano group in compound (IVa-1) or (IVb-1) to the carboxylic acid derivatives (IVa-2) or (IVb-2) can be carried out under an acidic condition (preferably strong acidic condition). An acid used for promoting of the reaction includes trichloroacetic acid, trifluoroacetic acid, p-toluenesulfonic acid, trifluoroborane etherate, methanesulfonic acid, sulfuric acid, hydrochloric acid, phosphoric acid, and polyphosphoric acid. The reaction temperature is generally about 25 to about 200° C., and preferably about 50 to about 120° C. The compound (IVa-1) or (IVb-2) is dissolved or suspended in 10 to 30-fold volume of an acid or a mixture of acid, and then the mixture is heated until the completion of the reaction.

The decarboxylation reaction may be conducted in an inert organic solvent such as aliphatic or aromatic hydrocarbon which may optionally be substituted with halogen, e.g. nonane, decane, dodecane, xylene, etc.; ether, e.g. ethylene glycol monobutyl ether, diethylene glycol dibutyl ether, etc.; sulfoxide, e.g. dimethyl sulfoxide, etc.; and sulfone, e.g. tetramethylene sulfone, etc. Also, this reaction can be carried out in the presence of a carboxylic acid containing mercapto group such as mercaptoacetic acid or thiosalicylic acid. The reaction temperature is about 150 to about 300° C., preferably about 160 to 250° C. The compound (IVa-2) or (IVb-2) is dissolved or suspended in the solvent, and then heated to provide the compound (I).

When $R^4$ in (IVb-2) is hydrogen, the reaction gives (Ib). This process can be carried out generally in accordance with the procedure described in Journal of Medicinal Chemistry, 22, 1483, 1979.

Process b)

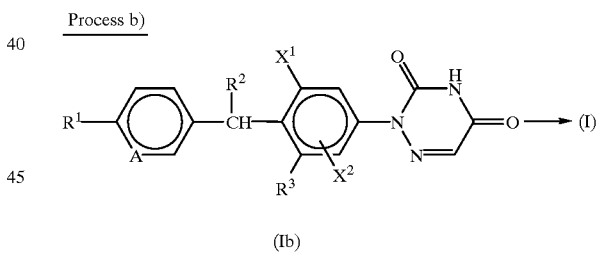

(Ib)

wherein $R^1$, A, $X^1$, $X^2$, $R^2$, and $R^3$ are as defined hereinbefore.

In this process b), a compound (Ib) is reacted with an acylating agent or an alkylating agent to provide the compound (I).

The acylating agent mentioned above includes formic acetic anhydride, acetic anhydride, propionic anhydride, acetyl chloride, and propionyl chloride. The alkylating agent includes dimethyl sulfate, alkyl halides such as methyl bromide, methyl iodide, ethyl bromide, ethyl iodide, isopropyl bromide, isopropyl iodide, propyl bromide, propyl iodide, etc., and formalin.

This reaction is generally carried out in an inert solvent or in the absence of a solvent and may be conducted in the presence of a base. The reaction temperature is generally about −10° C. to 100° C. and preferably about 0° to 0° C. The reaction may be conducted for a period of about 5 minutes to about 3 hours, preferably about 30 minutes to about 1 hour. The reaction solvent that can be used includes all of substantially inert solvents, i.e. the solvents in routine use for organic chemical reactions, such as aliphatic or aromatic hydrocarbons (e.g. benzene, ligroin, benzin, toluene, xylene, etc.), halogenated hydrocarbons (e.g. methylene chloride, ethylene chloride, chloroform, carbon tetrachloride, dichloroethane, chlorobenzene, o-dichlorobenzene, etc.), ethers (e.g. dibutyl ether, glycol dimethyl ether, diglycol dimethyl ether, tetrahydrofuran, dioxane, etc.), ketones (e.g. methyl ethyl ketone, methyl isopropyl ketone, methyl isobutyl ketone, etc.), esters (e.g. ethyl acetate etc.), nitriles (e.g. acetonitrile, propionitrile, etc.), amides (e.g. N,N-dimethylformamide, N,N-dimethylacetamide, hexamethyl-phosphoric triamide, etc.), N-methylpyrrolidone, dimethyl sulfoxide, and tetramethylene sulfone.

The base that can be used includes metal salts such as sodium hydride, sodium methoxide, sodium ethoxide, n-butyllithium, calcium hydride, etc. and organic bases such as (1,8-diazabicyclo[5.4.0]-7-undecene) (DBU), 1,1,3,3-tetramethylguanidine, etc.

The 1,2,4-triazine-3,5(2H,4H)-dione derivative (Ib), among the compounds of the present invention, can be produced with high efficiency by the following process (JP-A 325210/1996) besides processes as mentioned above.

Thus, hydrazone derivative (IVc), wherein $R^1$, A, $X^1$, $X^2$, $R^2$, and $R^3$ are as defined hereinbefore; $R^5$ and $R^6$ independently represent hydrogen, a hydrocarbon residue which may be substituted, or an electron attracting group; $R^7$ represents an alkyl group which may optionally be substituted, is reacted with a 2,2-dialkoxyethyl isocyanate to provide an intermediate, viz. semicarbazone derivative (V). The hydrocarbon residue which may be substituted, or an electron attracting group for $R^5$ and $R^6$, and the alkyl group which may optionally be substituted for $R^7$ are mentioned in detail hereinafter. This reaction is generally carried out in an inert solvent or in the absence of a solvent, optionally in the presence of a base. The reaction temperature depends on the species of solvent used but is generally about −20° C. to about 110° C. and preferably about 0° to about 50° C. The reaction time, which depends on the species of solvent used, is generally about 10 minutes to 5 hours and preferably 30 minutes to 2 hours.

The reaction solvent which can be used includes all of substantially inert solvents, i.e. the solvents in routine use for organic chemical reactions, such as aliphatic or aromatic hydrocarbons (e.g. benzene, ligroin, benzin, toluene, xylene, etc.), halogenated hydrocarbons (e.g. methylene chloride, ethylene chloride, chloroform, carbon tetrachloride, dichloroethane, chlorobenzene, o-dichlorobenzene, etc.),

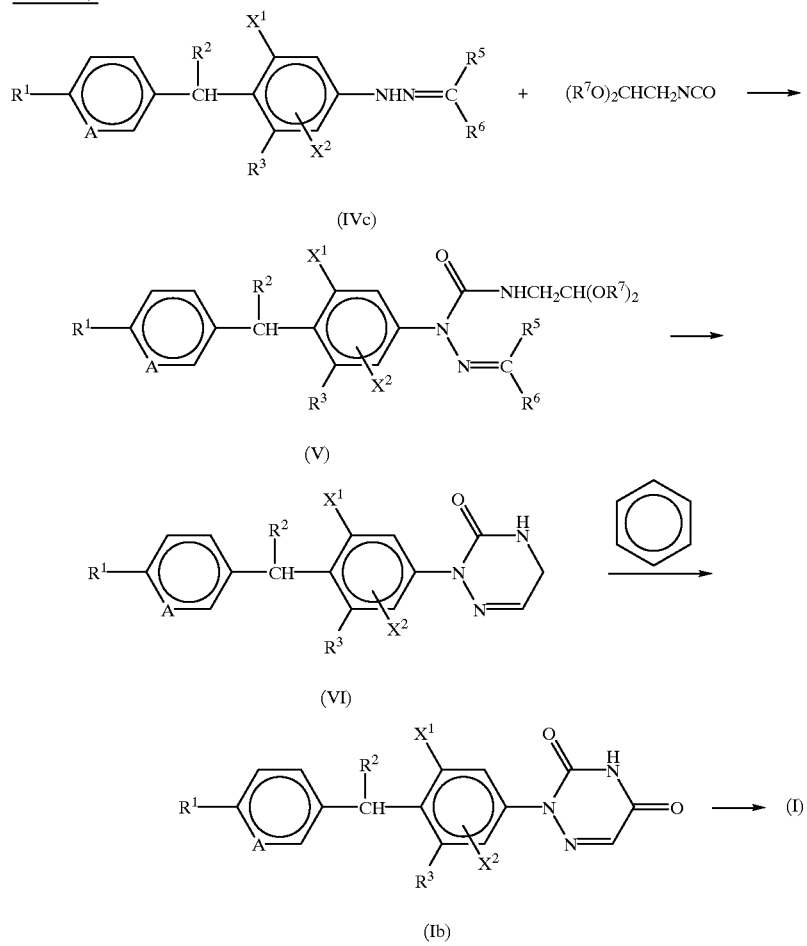

Process c)

ethers (e.g. diethyl ether, diisopropyl ether, dibutyl ether, glycol dimethyl ether, diglycol dimethyl ether, tetrahydrofuran, dioxane, etc.), ketones (e.g. acetone, methyl ethyl ketone, methyl isopropyl ketone, methyl isobutyl ketone, etc.), esters (e.g. ethyl acetate etc.), nitrites (e.g. acetonitrile, propionitrile, etc.), amides (e.g. N,N-dimethylformamide, N,N-dimethylacetamide, hexamethylphosphoric triamide, etc.), dimethyl sulfoxide, and pyridine.

The ratio of the 2,2-dialkoxyethyl isocyanate to the hydrazone derivative (IVc) is generally 1.0 to 3.5 molar equivalents and preferably 1.0 to 1.5 molar equivalents.

The base which can be used for promoting the reaction includes inorganic bases such as sodium carbonate, potassium carbonate, calcium carbonate, sodium hydroxide, potassium hydroxide, etc. and organic bases such as triethylamine, pyridine, dimethylaniline, picoline, 1,5-diazabicyclo[4.3.0]non-5-ene, 1,4-diazabicyclo[2.2.2]octane, DBU, etc. The proportion of the base is generally 0.001 to 30.0%, and preferably 0.01 to 5.0% with respect to the starting compound (IVc).

The semicarbazone derivative (V) thus synthesized is cyclized to provide a 2-substituted-1,2,4-triazin-3-one derivative (VI).

This reaction is generally carried out in an inert solvent or in the absence of a solvent and may be conducted in the presence of an acid. The reaction temperature depends on the type of solvent used but is generally about $-20°$ C. to $150°$ C. and preferably about $0°$ to $80°$ C. The reaction time, which depends on the species of solvent used, is generally about 10 minutes to 5 hours and preferably 30 minutes to 2 hours.

The reaction solvent which can be used includes all of substantially inert solvents, i.e. the solvents in routine use for organic chemical reactions, such as aliphatic or aromatic hydrocarbons (e.g. benzene, ligroin, benzin, toluene, xylene, etc.), halogenated hydrocarbons (e.g. methylene chloride, ethylene chloride, chloroform, carbon tetrachloride, dichloroethane, chlorobenzene, o-dichlorobenzene, etc.), ethers (e.g. diethyl ether, diisopropyl ether, dibutyl ether, glycol dimethyl ether, diglycol dimethyl ether, tetrahydrofuran, dioxane, etc.), ketones (e.g. acetone, methyl ethyl ketone, methyl isopropyl ketone, methyl isobutyl ketone, etc.), esters (e.g. ethyl acetate etc.), nitriles (e.g. acetonitrile, propionitrile, etc.), amides (e.g. N,N-dimethylformamide, N,N-dimethylacetamide, hexamethylphosphoric triamide, etc.), alcohols (e.g. methanol, ethanol, propanol, isopropyl alcohol, etc.), pyridine, and dimethyl sulfoxide.

The acid used for promoting this reaction includes trichloroacetic acid, trifluoroacetic acid, p-toluenesulfonic acid, boron trifluoride etherate, methanesulfonic acid, sulfuric acid, hydrochloric acid, phosphoric acid, and polyphosphoric acid.

The reaction mixture thus obtained can be used as it is, bypassing a step for isolating the semicarbazone derivative (V), for the next cyclization reaction to give the objective 1,2,4-triazin-3-one derivative (VI) in good yield. This reaction procedure (one-pot reaction) can be utilized with advantage in the commercial production of the compound (I).

Referring to the above formulas, the hydrocarbon residue which may be substituted as mentioned for $R^5$ and $R^6$ includes alkyl which may be substituted, aromatic homocyclic group which may optionally be substituted, and 5- or 6-membered aromatic heterocyclic group which may optionally be substituted. The alkyl group which may optionally be substituted includes the same species as those mentioned hereinafter for the alkyl group which may optionally be substituted for $R^7$. Preferably, the alkyl is lower($C_{1-4}$)alkyl, the aromatic homocyclic group is phenyl, and the aromatic heterocyclic group is pyridyl (e.g. 2-, 3-, or 4-pyridyl).

The substituent of the aromatic homocyclic group or a 5- or 6-membered aromatic heterocyclic group includes (1) a $C_{1-6}$ alkyl group (e.g. methyl, ethyl, etc.), (2) a $C_{2-6}$ alkenyl group (e.g. allyl, isopropenyl, isobutenyl, etc.), (3) a $C_{2-6}$ alkynyl group (e.g. propargyl, 2-butynyl, 3-butynyl, etc.), (4) a $C_{1-6}$ alkoxy group (e.g. methoxy, ethoxy, etc.), (5) an acyl group selected from the group consisting of a $C_{1-7}$ alkanoyl group (e.g. formyl, acetyl, propionyl, etc.), a $C_{6-14}$ aryl-carbonyl group (e.g. benzoyl, etc.), a $C_{1-6}$ alkoxy-carbonyl group (e.g. methoxycarbonyl, etc.), a $C_{6-14}$ aryloxy-carbonyl group (e.g. phenoxycarbonyl, etc.), a $C_{7-19}$ aralkyl-carbonyl group (e.g. phenyl-$C_{1-2}$ alkyl-carbonyl such as benzylcarbonyl, etc.), and $C_{7-19}$ aralkyloxycarbonyl (e.g. benzyloxycarbonyl, etc.), (6) nitro, (7) amino, (8) hydroxy, (9) cyano, (10) sulfamoyl, (11) mercapto, (12) halogen and (13) a $C_{1-4}$ alkylthio group (e.g. methylthio, ethylthio, etc.).

The number of the substituent is preferably 1 to 3.

The electron attracting group for $R^5$ and $R^6$ includes cyano, hydroxycarbonyl, a $C_{1-6}$ alkyl-oxycarbonyl group such as methoxycarbonyl, ethoxycarbonyl, etc., a $C_{6-10}$ aryl-oxycarbonyl group such as phenyloxycarbonyl, naphthyloxycarbonyl, etc., a 5- or 6-membered heterocycle-oxycarbonyl group in which the 5- or 6-membered heterocycle contains 1 to 4 hetero atoms selected from among a nitrogen atom, a sulfur atom, and an oxygen atom besides a carbon atom, such as pyridyloxycarbonyl, thienyloxycarbonyl, etc., a $C_{1-6}$ alkylsulfonyl group which may optionally be substituted with 1 to 3 halogen atoms (e.g. Cl, Br, F), such as methylsulfonyl, trifluoromethylsulfonyl, ethylsulfonyl, etc., aminosulfonyl, a di-$C_{1-4}$ alkoxyphosphoryl group such as dimethoxyphosphoryl, diethoxyphosphoryl, dipropoxyphosphoryl, etc., a $C_{1-6}$ acyl group such as acetyl, propionyl, etc., which may optionally be substituted with 1 to 3 halogens (e.g. Cl, Br, F), carbamoyl, and a $C_{1-6}$ alkyl-sulfonylthiocarbamoyl such as methylsulfonylthiocarbamoyl, ethylsulfonylthiocarbamoyl, etc.

$R^5$ and $R^6$ may form a $C_{4-7}$ cycloalkane ring taken together with the adjacent carbon atom.

The alkyl group of the alkyl group which may optionally be substituted for $R^7$ includes a $C_{1-4}$ alkyl group such as methyl, ethyl, propyl, or isopropyl. The substituent of the alkyl group for $R^7$ includes a $C_{1-4}$ alkylthio group (e.g. methylthio, ethylthio, etc.), halogen (e.g. fluorine, chlorine, bromine, iodine), a $C_{1-6}$ alkoxy group (e.g. methoxy, ethoxy, propoxy, etc.), nitro, $C_{1-6}$ alkoxy-carbonyl group (e.g. methoxycarbonyl, ethoxycarbonyl, propoxycarbonyl, etc.), mono- or di-$C_{1-6}$ alkylamino group (e.g. methylamino, ethylamino, dimethylamino, etc.), a $C_{1-6}$ alkoxyimino group (e.g. methoxyimino, etc.) and hydroxyimino.

The number of the substituents is preferably 1 to 3. $R^7$ is preferably ethyl or methyl.

The compound (VI), thus obtained, is oxidized by the routine procedure to provide the compound (Ib). The oxidation reaction is generally conducted in an inert solvent or in the absence of a solvent. The reaction temperature is generally about $-20$ to about $110°$ C. and preferably about 0 to about $50°$ C. For this reaction, virtually any inert organic solvent can be employed. Thus, it may can be any of the reaction solvents which are generally used in organic chemistry, for example, aliphatic or aromatic hydrocarbons (e.g. benzene, ligroin, benzine, toluene, xylene, etc.), halogenated hydrocarbons (e.g. methylene chloride, ethylene chloride, chloroform, carbon tetrachloride, dichloroethane, chlorobenzene, o-dichlorobenzene, etc.), ethers (e.g. diethyl ether, diisopropyl ether, dibutyl ether, glycol dimethyl ether, diglycol dimethyl ether, tetrahydrofuran, dioxane, etc.), ketones (e.g. acetone, methyl ethyl ketone, methyl isopropyl ketone, methyl isobutyl ketone, etc.), esters (e.g. ethyl acetate etc.), nitriles (e.g. acetonitrile, propionitrile, etc.), amides (e.g. dimethylformamide, dimethylacetamide, hexamethylphosphorotriamide, etc.), dimethylsulfoxide, pyridine, and so on. This reaction can be carried out by using a suitable oxidant. The oxidant includes permanganate, chromic acid, mercury (II) acetate, oxygen, ozone, hydrogen peroxide, or organic peracid (e.g. perbenzoic acid, metachloroperbenzoic acid, monoperoxyphthalic acid, performic acid, peracetic acid, trifluoroperacetic acid, etc.). The amount of oxidant used for this process is 1.0 to 5.0 molar equivalents and preferably 1.0 to 3.5 molar equivalents with respect to the starting compound (VI). Then, the compound (Ib) thus obtained is subjected to a substitution reaction to provide the compound (I). Optionally, the compound (I) can be converted to various physiologically acceptable salts, e.g. salts with alkali metals such as sodium and potassium, salts with alkaline earth metals such as calcium, salts with inorganic acids such as phosphoric acid, nitric acid, and sulfuric acid, and organic acids such as acetic acid and succinic acid, in the per se known manner.

The hydrazine derivative (X) for use as a starting compound in accordance with the invention can be produced with high efficiency by the following process [JP-A 337576/1996].

Process d)

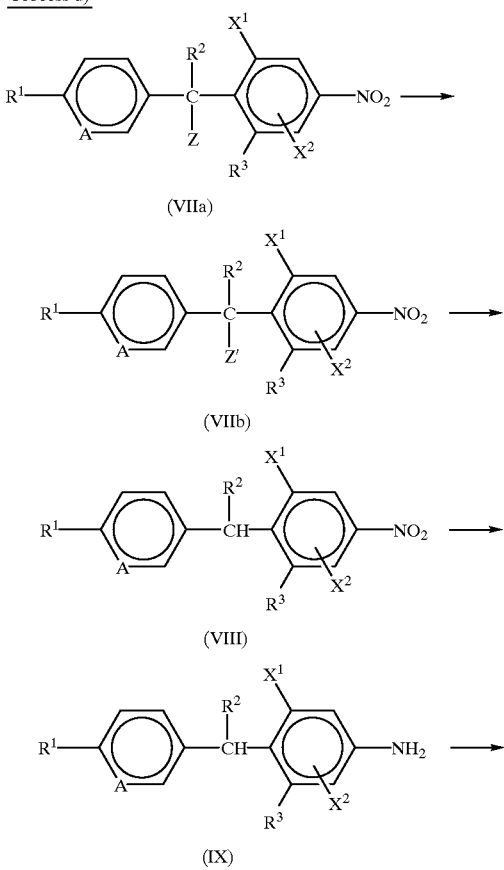

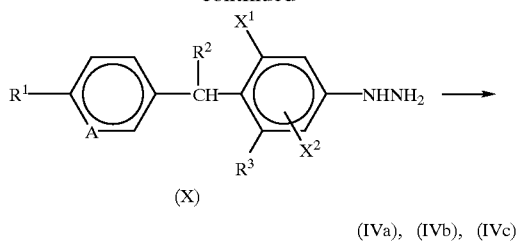

wherein Z represents a carboxylic acid ester residue or cyano; Z' represents carboxy or amido.

The carboxylic acid ester includes methyl carboxylic acid ester, ethyl carboxylic acid ester, n-propyl carboxylic acid ester, isopropyl carboxylic acid ester or phenyl carboxylic acid ester.

In this process d), the starting nitro compound (VIIa) is hydrolyzed to provide the compound (VIIb) which is, then, subjected to decarboxylation to provide the compound (VIII). This compound (VIII) is reduced to provide the amino compound (IX).

The process from the compound (VIIa) to the compound (VIII) is generally conducted in a polar solvent containing a small proportion of water under slightly alkaline or neutral conditions in the presence of a halide ion or an alkali metal salt. The reaction temperature is generally about 40° to 200° C. and preferably about 70° C. to 150° C.

The solvent which can be used for the above reaction includes all of substantially polar organic solvents, i.e. the solvents in routine use for organic chemical reactions such as alcohols (e.g. methanol, ethanol, etc.), nitriles (e.g. acetonitrile, propionitrile, etc.), amides (e.g. N,N-dimethylformamide, N,N-dimethylacetamide, hexamethylphosphoric triamide, etc.), N-methylpyrrolidone, dimethyl sulfoxide, tetramethylene sulfone, etc.

To accelerate the reaction, at least one halide ion donor compound, e.g. an alkali metal salt such as NaF, NaCl, NaBr, NaI, LiCl, LiBr, KF, KCl, KBr, NaCN, KCN, or $CaF_2$, tetramethylammonium bromide, 1,5-diazabicyclo[4.3.0]non-5-ene.HBr, 1,4-diazabicyclo[2.2.2]octane.HBr, 1,8-diazabicyclo[5.4.0]undec-7-ene (DBU).HBr, or 1,8-diazabicyclo[5.4.0]undec-7-ene.HCl can be used generally in a proportion of 1.0 to 5.0 molar equivalents with respect to the compound (VIIb).

The amount of water used in the production process from compound (VIIa) to (VIIb) is generally 1.0 to 20.0 molar equivalents and preferably 3.0 to 6.0 molar equivalents with respect to the starting compound.

The decarboxylation reaction from the compound (VIIb) to (VIII) is conducted in a polar solvent as mentioned above or in the absence of a solvent. This reaction can be carried out in the presence of a halide ion donor compound or an alkali metal salt as mentioned above. When this reaction is conducted in a polar solvent, pH of the reaction system is preferably 6 to 8. The reaction temperature is generally about 40° C. to 200° C., preferably about 100° C. to 150° C.

The compound (IX) can be quantitatively synthesized from the compound (VIII) by the conventional reduction reaction, e.g. catalytic reduction or Bechamp reduction [Shin Jikken Kagaku Koza (New Experimental Chemistry Series), Vol. 15 (II), Maruzen, 1977]. Subjecting this compound (IX) to diazotization or reduction reaction gives the hydrazine derivative (X).

Process e)

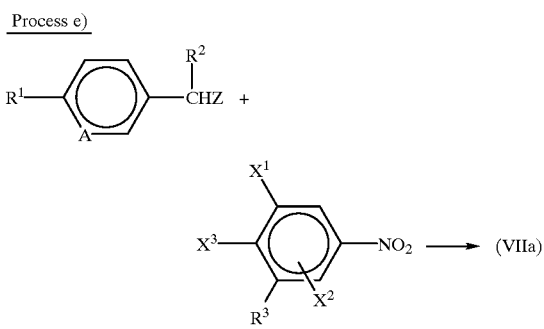

wherein $R^1$, A, $R^2$, $R^3$, $X^1$, $X^2$, and Z are as defined hereinbefore; $X^3$ represents halogen.

In the above process e), a carboxylic acid derivative and a 4-halonitrobenzene are subjected to a condensation reaction in the presence of a suitable base to provide the compound (VIIa), i.e. the starting compound for the process d) described above. The compound (VIII) can be obtained in good yield in a one-pot reaction system without prior isolation of the compound (VIIa) synthesized by this process e). The reaction conditions may be similar to those described just above but since a base such as an alkali metal salt or a quaternary ammonium salt is used as a dehalogenating agent in the first-step condensation reaction, the necessary halide ion or alkali metal ion is already available in the reaction system so that the base such as said alkali metal salt or quaternary ammonium salt need not be supplied de novo at the reaction of (VIIa) to (VIII).

Process f)

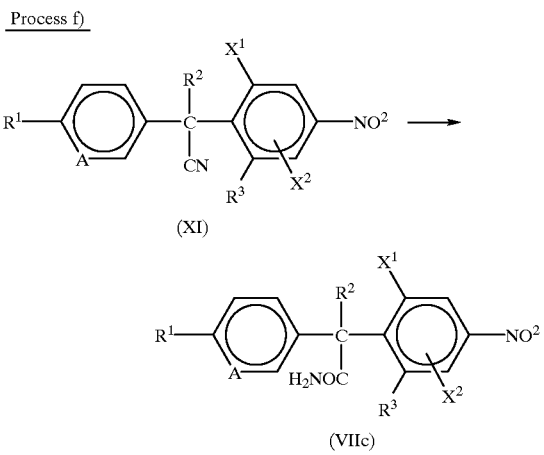

wherein $R^1$, A, $X^1$, $X^2$, $R^2$, and $R^3$ are as defined hereinbefore.

In this process f), the acetonitrile derivative (XI) prepared by the known method (e.g. J. W. McFarland, et al., J. Med., Chem., 34, 1908, 1991) is hydrolyzed with an acid or a Lewis acid, such as concentrated sulfuric acid, hydrochloric acid, polyphosphoric acid, formic acid, titanium tetrachloride, etc., to provide the amide compound (VIIc), i.e. the starting compound for the process d) described just above.

The compound (I) or a salt thereof of the invention is effective in the control of harmful parasitic protozoa in the breeding of animals including vertebrate animals such as mammals, fowls and fish, and insects, showing anti-protozoal activity against any and all stages of growth of such protozoa. Moreover, compound (I) and a salt thereof of the present invention have sufficiently useful anti-protozoal activity against protozoa including susceptible strains or including strains resistant to the conventional chemicals. As a result, the compound (I) contributes to increased productivity in animal production (e.g. the productivity of meat, milk, fur, skin, eggs, honey, etc. as well as the bleedability of animals). Moreover, a more economical breeding of animals can be insured through use of the compound (I) of the present invention.

A broad spectrum of protozoa can be controlled with the compound of the invention. Among such protozoa may be mentioned those of the phylum Apicomplexa, for example protozoa of the family Eimeriidae such as protozoa of the genus Eimeria, specifically *E. acervulina, E. adenoides, E. alabahmensis, E. arloingi, E. auburnensis, E. bovis, E. brunetti, E. canis, E. contorta, E. ellipsoidales, E. falciformis, E. gallopavonis, E. hagani, E. intestinalis, E. magna, E. maxima, E. meleagridis, E. meleagrimitis, E. mitis, E. mivati, E. necatrix, E. ninakohlyakimovae, E. ovis, E. parva, E. pavonis, E. perforans, E. piriformis, E. praecox, E. stiedai, E. suis, E. tenella, E. truncata,* and *E. zuernii*; protozoa of the genus Isospora, e.g. *I. belli, I. canis, I. felis, I. rivolta,* and *I. suis*; Cryptosooridium, *Toxoplasma gondii,* protozoa of the family Sarcocystidae such as *Sarcocystis bovicanis, S. bovihominis, S. ovicanis, S. ovifelis,* and *S. suihominis*; protozoa of the genus Leucocytozoon such as *L. simondi* and *L. caullervi*, protozoa of the family Plasmodiidae such as *Plasmodium berahei, P. falciparum, P. malariae,* and *P. ovale*; protozoa of the subclass Piroplasmea; protozoa of the genus Babesia such as *B. argentina, B. bovis,* and *B. canis*; protozoa of the genus Theileria such as *T. parva*; Adeleina, *Hepatozoon canis,* etc.; protozoa of the subphylum Mvxospora and of the subphylum Microspora; and protozoa of the genus Glugea and of the genus Nosema.

The compound (I) or a salt thereof, can be used for both prophylactic and therapeutic purposes in various protozoal infections in vertebrate animals such as mammals (e.g. cattle, horse, hog, sheep, goat, camel, buffalo, donkey, rabbit, deer, reindeer, mink, chinchilla, raccoon, mouse, rat, guinea pig, golden hamster, dog, cat, human, etc.), fowls (e.g. chicken, quail, goose, turkey, duck, mallard, pigeon, etc.), and fresh water and seawater fishes (e.g. carp, eel, trout, sweet fish, catfish, salmon, sea bream, yellowtail, tiger puffer, tongue sole, flatfish, etc.) or insects (e.g. bee).

The compound (I) or a salt thereof, can be safely administered, either as it is or in various dosage forms, whether orally or otherwise. Such dosage forms can be prepared by the per se known procedures (e.g. JP-A 1047/1993, JP-A 117250/1193, JP-A 240003/1990, JP-A 61972/1987).

For administration into the digestive canal of the host, the composition can be administered orally in such dosage forms as bulk powders, powders (inclusive of soluble powders), tablets, capsules, paste, liquid, granules, crumbles, pellets, etc., either as such or in admixture with feed or drinking water. For administration to the skin, the composition can be applied by dipping, spraying, washing, dripping, or coating. For non-oral administration, the composition can be used in the form of an injection (e.g. intramuscular, subcutaneous, intravenous, or intraperitoneal injection). The dosage form thus includes various liquids such as injectable solutions, oral liquids, liquids for application to the skin or into body cavities, drips, gels, emulsions and suspensions for oral administration, parenteral administration, or application to the skin, semisolids, ointments, powders, granules, pellets, tablets, capsules, aerosols or inhalants, and shaped articles containing the compound (I) or a salt thereof.

Injectable solutions can be prepared by dissolving the compound (I) or a salt thereof in a suitable vehicle, adding various optional additives such as a solubilizer, an isotonizing agent, e.g. an acid, a base or a buffer, an antioxidant, and an antiseptic, sterilizing the mixture and packing it into vials. The vehicle that can be used includes a variety of physio- logically acceptable solvents, e.g. water, alcohols such as ethanol, butanol, benzyl alcohol, etc., glycerol, hydrocarbons, propylene glycol, polyethylene glycol, N-methylpyrrolidone, and mixtures of such solvents. To prepare an injection, the compound of the present invention may be dissolved in a physiologically acceptable vegetable or synthetic oil for injection.

The solubilizer may be any substance that promotes dissolution or prevents precipitation of the compound (I) or a salt thereof in the solvent. Thus, for example, polyvinylpyrrolidone, polyethoxylated castor oil, polyoxyethylene sorbitan ester, etc. can be mentioned.

The antiseptic that can be used includes but is not limited to benzyl alcohol, trichlorobutanol, p-hydroxybenzoic esters, and n-butanol.

The oral liquid is provided either as a liquid which is administered as it is or in the form of a concentrate which is diluted to the dose concentration in the field and administered orally. Such an oral liquid can be manufactured by the established procedure.

The solution for application to the skin is administered to the skin by dripping, spreading, embrocating, washing, spraying, dipping, bathing, or cleansing. Such solutions can also be manufactured by the established procedures. It is advantageous to add thickeners in the course of preparation. The thickeners include but is not limited to such inorganic substances as bentonite, silica gel, aluminum monostearate, etc. and such organic substances as CMC sodium, other cellulose derivatives, polyvinyl alcohol and its copolymers, acrylates, and methacrylates.

Gels are applied to or coated on the skin or applied into body cavities. Gels can be manufactured by adding a sufficient amount of a thickener to a prepared solution to provide for an appropriate ointment-like consistency in the per se conventional manner. As the thickener, a variety of substances such as those mentioned above can be selectively employed.

The drip is topically applied to the skin by dripping or washing so that the active ingredient may penetrate the skin for a systemic effect or simply act on the skin surface.

The drip can be manufactured by dissolving, suspending, or emulsifying the compound (I) or a salt thereof in a suitable vehicle or vehicle mixture for transdermal delivery. The drip may be supplemented with various additives such as a coloring agent, an absorption promoter, an antioxidant, a light screen, and a thickener.

The vehicle that can be used includes water, alkanols, glycols, polyethylene glycol, polypropylene glycol, glycerol, aromatic alcohols such as benzyl alcohol, phenethyl alcohol, phenoxyethanol, etc., esters such as ethyl acetate, butyl acetate, benzyl benzoate, etc., ethers such as alkylene glycol alkyl ether, dipropylene glycol monomethyl ether, diethylene glycol monobutyl ether, etc., ketones such as acetone, methyl ethyl ketone, etc., aromatic and/or aliphatic hydrocarbons, vegetable and synthetic oils, N,N-dimethylformamide (DMF), N,N-dimethylacetamide, N-methylpyrrolidone, and 2-dimethyl-4-oxomethylene-1,3-dioxolane, among others.

The coloring agent may be any pigment or dye that can be dissolved or suspended and administered safely to animals.

The absorption promoter that can be used includes dimethyl sulfoxide (DMSO), extender oils, isopropyl myristate, dipropylene glycol pelargonate, silicone oil, fatty acid esters, triglycerides, and aliphatic alcohols.

The antioxidant includes sulfites, metabisulfites such as potassium metabisulfite, ascorbic acid, butylhydroxytoluene, butylhydroxyanisole, and tocopherol.

The light screen may for example be a benzophenone derivative.

The thickener includes cellulose derivatives, starch derivatives, polyacrylates, alginates, and gelatin.

The emulsion may be whichever of the oil-in-water type or the water-in-oil type, and can be prepared by dissolving the compound (I) or a salt thereof either in a hydrophobic solvent or in a hydrophilic solvent and homogenizing the solution in the presence of an emulsifier and other additives such as a coloring agent, an absorption promoter, antiseptic, an antioxidant, a light screen, and a thickener.

The hydrophilic solvent includes a variety of substances including paraffin oils, silicone oils, vegetable oils such as sesame oil, almond oil, castor oil, etc., synthetic triglycerides such as capryl/capric diglyceride, fatty acids of vegetable origin and their triglycerides, non-natural saturated or unsaturated fatty acids and the corresponding mono- and diglycerides, fatty acid esters such as ethyl stearate, n-butyryl adipate, hexyl laurate, dipropylene glycol pelargonate, etc., branched-chain fatty acid esters of $C_{16-17}$ saturated aliphatic alcohols, such as isopropyl myristate, isopropyl palmitate, etc., capryl/capric esters of $C_{12-18}$ saturated aliphatic alcohols, isopropyl stearate, oleyl oleate, decyl oleate, ethyl oleate, ethyl lactate, wax-like fatty acid esters such as dibutyl phthalate, diisopropyl adipate, etc., aliphatic alcohol esters of adipic acid, e.g. isotridecyl alcohol ester, 2-octyldodecanol ester, cetyl stearyl alcohol ester and oleyl alcohol ester, and fatty acids such as oleic acid.

The hydrophilic solvent includes water, alcohols such as propylene glycol, glycerol, sorbitol, etc., and mixtures of such solvents.

The emulsifier includes nonionic surfactants such as polyethoxylated castor oil, polyoxyethylene sorbitan monooleate, sorbitan monostearate, glycerol monostearate, polyoxyethylene stearate, and alkylphenol polyglycol ethers; amphoteric surfactants such as disodium N-lauryl-β-iminodipropionate, lecithin, etc., anionic surfactants such as sodium lauryl sulfate, aliphatic alcohol ether sulfates, mono- or dialkylpolyglycol ethers, orthophosphoric ester monoethanolamine salts, etc., and cationic surfactants such as cetyltrimethylammonium chloride, and so on.

For the purpose of stabilizing an emulsion, there may be added a thickener such as carboxymethylcellulose (CMC), methylcellulose (MC), other cellulose derivatives, starch derivatives, polyacrylates, alginic acid esters, gelatin, gum arabic, polyvinylpyrrolidone, polyvinyl alcohol, methyl vinyl ether-maleic anhydride copolymer, polyethylene glycol, waxes, silica gel, etc. in a suitable proportion.

When the antiprotozoal composition of the present invention is to be provided in the form of a suspension, such a suspension can be prepared by suspending the compound (I) or a salt thereof uniformly in a medium together with various auxiliary agents such as a wetting agent, a coloring agent, an absorption promoter, an antiseptic, an antioxidant, a light screen, etc.

As the wetting agent (dispersant), the surfactants mentioned above can be selectively added in a suitable proportion. The semisolid dosage form for oral administration or application to the skin can be prepared by admixing the compound (I) or a salt thereof with a suitable excipient, optionally together with other additives, and molding the resulting mixture.

The excipient may be any physiologically acceptable inert material, thus including various inorganic excipients such as sodium chloride, e.g. calcium carbonate and other carbonates, hydrogencarbonates, aluminum oxide, silic acid, silica gel, phosphates, etc. and organic excipients such as saccharides, cellulose, and feedstuffs such as powdered milk, cracked or crushed cereals, starches, and others.

The above-mentioned antiseptic, antioxidant, and coloring agent may also be added in suitable amounts. In addition, a lubricant such as magnesium stearate, stearic acid, talc, bentonite, etc., a disintegrator such as starch and crosslinked polyvinylpyrrolidone, and a binder such as starch, gelatin, polyvinylpyrrolidone, crystalline cellulose, etc. can also be added.

The antiprotozoal composition of the present present invention may contain more than one species of compound (I) or a salt thereof of the present invention, and barring the risk of interactions, may further contain, or may be used in combination with, other substances assisting in the promotion of animal health or sharing the prophylactic or therapeutic function with the compound of the present invention.

The antiprotozoal composition of the present invention is formulated or prepared so as to contain the compound (I) or its salt in a concentration ranging from about 0.01 ppm to about 1%, preferably about 0.1 ppm to 0.1%. In the case of a dosage form for use after dilution in the field, its concentration is about 0.01 to 90% or preferably about 0.1 to 30%.

Generally, the antiprotozoal composition of the present invention can be administered to an animal within the dose range of about 0.01 to about 50 mg/day, preferably about 0.1 to 5 mg/day, as the compound (I) or a salt thereof, per kilogram body weight of the recipient animal. For example, the compound (I) or a salt thereof can be incorporated in the animal diet at a level ranging from about 0.01 to about 100 ppm, preferably about 0.1 to 50 ppm. The medicated diet thus obtained can be used for both therapeutic and prophylactic purposes. Such a medicated diet can be generally provided by preparing a concentrate or premix containing generally about 0.5 to 30 weight %, preferably about 1 to 20 weight % of the compound (I) or a salt thereof together with the routine excipient for animal use and mixing it into the regular feedstuff. The excipient that can be used includes corn flour supplemented with a small proportion of edible oil, e.g. corn oil or soybean oil, for prevention of dust formation, corn, soybean meal, and mineral salts. The premix is evenly incorporated in the ration and fed to the animal.

For the treatment and prevention of sporozoasis in domestic fowls, particularly chicken, quail, duck, mallard, goose, and turkey, generally about 0.01 to 100 ppm or preferably about 0.1 to 50 ppm of the compound (I) or its salt is mixed into a suitable edible material such as a nutrient formula feed. Administration can also be made via drinking water.

For use in the treatment of animals, typically in the therapy of sporozoasis or toxoplasmosis in a mammal, about 0.5 to 100 mg/kg b. wt. of the compound (I) or a salt thereof is administered daily. The above dosage is not critical, however, and can be increased or decreased according to animal species and body weight, dosing method, individual response to treatment, formulation, dosing schedule, and other factors. For massive administration, the compound of the present invention can be conveniently administered in a few divided doses.

For application to fish, the composition is generally administered orally, for example via feed or by way of a "drug bath". The drug-bath method comprises transferring fish from a culture pond to a drug-containing bath and keeping them in the bath for a while (several minutes to a few hours). However, the whole habitat for fish (e.g. a pool, aquarium, tank, or pond) may be treated either on a temporary basis or permanently. In such applications, the compound (I) or a salt thereof can be used in a dosage form suitable for each treatment method. The concentration of the active ingredient in the composition is about 1 ppm to 10 weight %.

For use in a drug bath or in the omnibus treatment of the habitat (pool treatment), the antiprotozoal compound of the present invention is preferably provided in the form of a solution in a mixture of one or more polar solvents which can be diluted or dispersed with water. Such a solution is prepared by dissolving or suspending the compound (I) or a salt thereof in a water-soluble vehicle such as a polar solvent. The pH of the aqueous solution after addition of the compound (I) or a salt thereof is preferably pH 7–10, particularly about 8–10.

Since administration of the compound of the present invention results in successful control of protozoa and reduction in the incidence of associated diseases and death and consequent improvement in retarded growth and general condition, the composition can be used with advantage for preventing decrease of rearing production, e.g. the production of meat, milk, fur, eggs, honey, etc. Moreover, with the composition of the present invention, ornamental or pet animals, too, can be reared in good health.

The triazine derivative or a salt thereof of the present invention has high antiprotozoal activity with a high toxicological threshold insuring safety.

The following reference examples, examples, test example and formulation example are intended to illustrate the present invention in further detail and should by no means be interpreted as limiting its scope.

Inventors hereby incorporate by reference Japanese priority Application No. 230434-1996, filed Aug. 30, 1996, in its entirety.

EXAMPLES

Reference Example 1

Synthesis of 4-[4-(4-chlorobenzoyl)benzyl]-3,5-dichloronitrobenzene

In 15 ml of dichloromethane was suspended 1.30 g of AlCl3, and a solution of 1.43 g of 4-chlorobenzoyl chloride in 3 ml of dichloromethane was added to the suspension for a period of 30 minutes. A solution of 2.00 g of 4-benzyl-3,5-dichloronitrobenzene in 2 ml of dichloromethane was added for a period of 15 minutes, and the reaction mixture was refluxed for 22 hours. The reaction mixture was poured into 25 ml of ice-water, and 30 ml of chloroform and 3 ml of conc. hydrochloric acid were added. The resulting mixture was stirred for 15 minutes at a room temperature, and the organic layer was separated, washed with water and saturated aqueous sodium bicarbonate solution, dried and concentrated to quantitatively give the above-identified compound as oil.

$^1$H-NMR (90 MHz, CDCl$_3$, δ ppm); 4.49(2H,s), 7.22–7.78(8H,m), 8.24(2H,s)

Reference Example 2

Synthesis of 4-[4-(4-chlorobenzoyl)benzyl]-3,5-dichloroaniline

In 50 ml of ethyl acetate was dissolved 3.25 g of 4-[4-(4-chlorobenzoyl)benzyl]-3,5-dichloronitrobenzene, and 8.00 g of SnCl₃.2H₂O was added. The reaction mixture was refluxed for 1 hour, and then poured into ice-water. The mixture was alkalified with conc. ammonia solution, and the organic layer was collected by decantation. The aqueous layer was extracted twice with 50 ml of ethyl acetate, and the organic layers were combined, washed with water, dried and concentrated. The residue was purified by silica gel column chromatography (ethyl acetate/hexane=1/2) to give the above-identified compound as pale brown amorphous powder (yield: 70%).

$^1$H-NMR (90 MHz, CDCl₃, δ ppm); 3.75(2H,br-s), 4.27 (2H, s), 6.67(2H,s), 7.23–7.78(8H,m)

Reference Example 3

Synthesis of 1-benzylidene-2-{4-[4-(4-chlorobenzoyl)benzyl]-3,5-dichlorophenyl}hydrazine In 15 ml of acetic acid was dissolved 2.10 g of 4-[4-(4-chlorobenzoyl)benzyl]-3,5-dichloroaniline, and 1.8 ml of conc. hydrochloric acid was added. A solution of 0.41 g of NaNO₂ in 1 ml of water was dropwise added to the mixture with stirring at 5 to 10 üÄ for a period of 10 minutes. The pale brown mixture was stirred at the same temperature for 1 hour, and then 0.60 g of benzaldehyde was added. A solution of 3.36 g of SnCl₂.2H₂O in 3.4 ml of conc. hydrochloric acid was added for a period of 15 minutes, and the resulting mixture was reacted at 20 to 25° C. for 3 hours. Precipitated crystals were collected by filtration and recrystallized from ethyl acetate to give the above-identified compound as yellow cryatals (yield: 40%).

m.p.; 215–216° C.; $^1$H-NMR (90 MHz, CDCl₃, δ ppm); 4.32(2H,s), 7.12(2H,s), 7.25–7.78(15H,m)

Reference Example 4

Synthesis of 1-benzylidene-2-{4-[4-(4-chlorobenzoyl)benzyl]-3,5-dichlorophenyl}-4-(2,2-dimethoxy)ethyl semicarbazide In 15 ml of acetonitrile was suspended 1.00 g of 1-benzylidene-2-{4-[4-(4-chlorobenzoyl)benzyl]-3,5-dichlorophenyl}hydrazine, and 0.40 g of 2,2-dimethoxyethyl isocyanate was added, and then 15 ml of DBU(1,8-diazabicyclo[5.4.0]undec-7-ene) was added. The mixture was reacted at 20 to 25° C. for 1 hour, and precipitated crystals were collected by filtration to give the above-identified compound as colorless crystals (yield: 75%).

m.p.; 158–160° C.; $^1$H-NMR (90 MHz, CDCl₃, δ ppm); 3.47–3.60(8H,m), 4.46(2H,s), 4.52(1H,t), 6.92(1H,t), 7.29–7.80(16H,m)

Reference Example 5

Synthesis of 2-{4-[4-(4-chlorobenzoyl)benzyl]-3,5-dichlorophenyl}-4,5-dihydro-1,2,4-triazin-3(2H)-one In 12 ml of acetonitrile was suspended 0.90 g of 1-benzylidene-2-{4-[4-(4-chlorobenzoyl)benzyl]-3,5-dichlorophenyl}-4-(2,2-dimethoxy)ethyl semicarbazide, and 0.15 g of conc. hydrochloric acid was added. The mixture was reacted at 20 to 25° C. for 1 hour, and precipitated crystals were collected by filtration to give the above-identified compound as colorless crystals (yield: 96%).

m.p.; 205–206° C.; $^1$H-NMR (90 MHz, CDCl₃, δ ppm); 4.11–4.16(2H,m), 4.38(2H,s), 5.67(1H,br-s), 7.05–7.15(lH, m), 7.25–7.78(10H,m)

Example 1

Synthesis of 2-{4-[4-(4-chlorobenzoyl)benzyl-3,5-dichlorophenyl}-1,2,4-triazine-3,5(2H,4H)-dione In 20 ml of dichloromethane was dissolved 0.473 g of 2-{4-[4-(4-chlorobenzoyl)benzyl]-3,5-dichlorophenyl}-4,5-dihydro-1,2,4-triazine-3(2H)-one followed by addition of 1.0 g of pyridinium chlorochromate, and the mixture was stirred at room temperature for 12 hours. After completion of the reaction, the reaction mixture was filtered to remove the insoluble substance. The filtrate was concentrated and purified by silica gel chromatography (ethyl acetate/hexane= 2/1) to provide 210 mg of the title compound as colorless crystals.

m.p.; 204–205° C.; $^1$H-NMR (90MHz, CDCl₃, δ ppm): 4.43(2H,s), 7.30–7.79(11H,m), 8.70(1H,b)

Example 2

Synthesis of 2-[4-(4-benzylbenzyl)-3,5-dichlorophenyl]-1,2,4-triazine-3,5(2H,4H)-dione In 20 ml of dichloromethane was dissolved 438 mg of 2-[4-(4-benzylbenzyl)-3,5-dichlorophenyl]-4,5-dihydro-1,2, 4-triazine-3(2H)-one followed by addition of 1.0 g of pyridinium chlorochromate, and the mixture was stirred at room temperature for 12 hours. After completion of the reaction, the reaction mixture was filtered to remove the insoluble substance. The filtrate was concentrated and purified by silica gel chromatography (ethyl acetate/hexane=2/1) to provide 230 mg of the title compound as colorless crystals.

m.p.; 164–165° C.; $^1$H-NMR (90MHz, CDCl₃, δ ppm): 3.92(2H,s), 4.29(2H,s), 7.09(5H,m), 7.20(s,4H), 7.55(s,1H), 7.59(s,2H), 9.67(1H,b)

Example 3

The compounds synthesized by the same procedure as described in Reference Examples 1 to 5, Example 1 and 2 and their physical constants are shown in Table 1 to 4.

TABLE 1
| No. | Compound | Melting Point (° C.) | ¹H-NMR [solvent] δ |
|---|---|---|---|
| 1 | 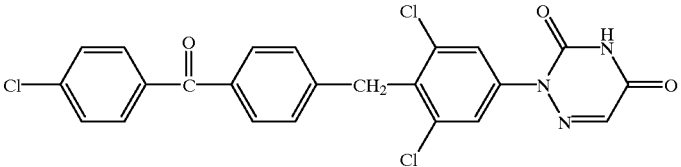 | 204~205 | [CDCl₃] 4.43(s, 2H), 7.30~7.79(m, 11H), 8.70(br, 1H). |
| 2 | 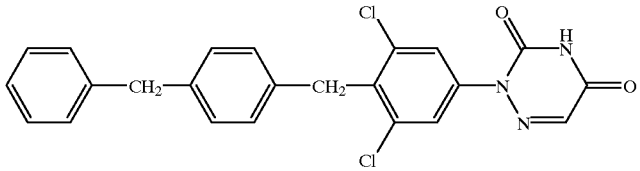 | 164~165 | [CDCl₃] 3.92(s, 2H), 4.29(s, 2H), 7.09 (s, 5H), 7.20(s, 4H), 7.55(s, 1H), 7.59 (s, 2H), 9.67(br, 1H). |
| 3 | 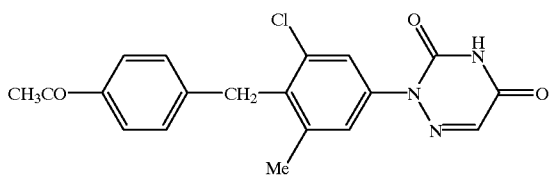 | caramelo | [CDCl₃] 2.30(s, 3H), 2.56(s, 3H), 4.28 (s, 2H), 7.13~7.91(m, 7H), 8.67(br, 1H). |
| 4 | 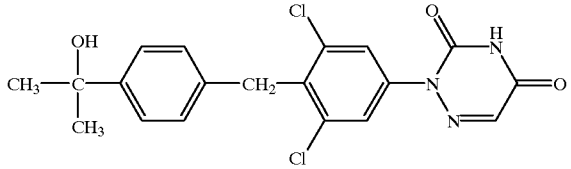 | 168~169 | [CDCl₃] 1.56(s, 6H), 1.75(s, 1H), 4.33 (s, 2H), 7.17(d, 2H), 7.40(d, 2H), 7.57 (s, 1H), 7.62(s, 2H), 8.90(br, 1H). |
| 5 | 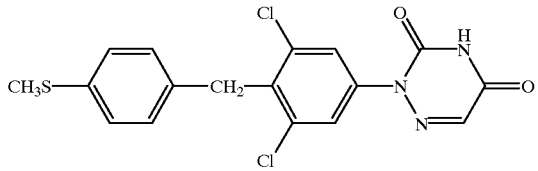 | 141~142 | [CDCl₃] 2.44(s, 3H), 4.28(s, 2H), 7.14 (s, 4H), 7.60(br.s, 3H), 9.45(br, 1H). |
| 6 | 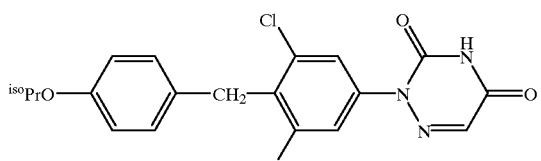 | 155~156 | [CDCl₃] 1.28(d, 6H), 4.24(s, 2H), 4.47 (q, q, 1H), 6.93(q, 4H), 7.56(s, 1H), 7.58(s, 2H), 9.41(br, 1H). |
| 7 | 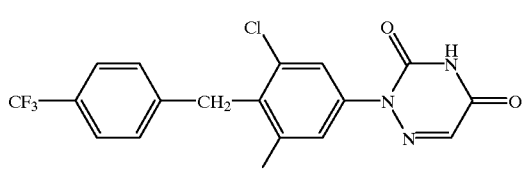 | 125~126 | [CDCl₃] 4.28(s, 2H), 7.09(s, 4H), 7.58 (s, 1H), 7.59(s, 2H), 8.80(br, 1H). |

TABLE 2

| # | Structure | mp (°C) | NMR |
|---|---|---|---|
| 8 | (structure) | caramelo | [CDCl₃] 1.48(d, 3H), 1.83(br, 1H), 2.31(s, 3H), 4.21(s, 2H), 4.86(q, 1H), 7.06(d, 2H), 7.23~7.31 (m, 3H), 7.51(d, 1H), 7.55(s, 1H), 8.95(br, 1H). |
| 9 | (structure) | 206~207 | [DMSO-d₆] 2.11(s, 3H), 4.31(s, 2H), 7.37(q, 4H), 7.70(s, 1H), 7.72(s, 2H), 11.14(s, 1H), 12.45(s, 1H). |
| 10 | (structure) | caramelo | [CDCl₃] 4.42(s, 2H), 7.31(d, 2H), 7.60(s, 1H), 7.67(s, 2H), 8.18(d, 2H), 8.98(br, 1H). |
| 11 | (structure) | 175~176 | [CDCl₃] 4.38(s, 2H), 6.61(t, 1H), 7.35(q, 4H), 7.61(s, 1H), 7.65(s, 2H), 9.56(br, 1H). |
| 12 | (structure) | 236~237 | [DMSO-d₆] 3.18(s, 3H), 4.42(s, 2H), 7.64(q, 4H), 7.70(s, 1H), 7.75(s, 2H), 12.48(s, 1H). |
| 13 | (structure) | 161~162 | [CDCl₃] 1.90(t, 3H), 4.37(s, 2H), 7.33(q, 4H), 7.60(s, 1H), 7.65(s, 2H), 8.75(br, 1H). |
| 14 | (structure) | 152~154 | [CDCl₃] 2.11(s, 3H), 4.34(s, 2H), 5.03(t, 1H), 5.33(s, 1H), 7.15(d, 2H), 7.38(d, 2H), 7.58(s, 1H), 7.62(s, 2H), 8.69(br, 1H). |
| 15 | (structure) | 186~187 | [CDCl₃] 2.19(s, 3H), 3.97(s, 3H), 4.35(s, 2H). 7.13~7.63(m, 7H), 8.70(br, 1H). |

TABLE 3

| # | Structure | mp (°C) | NMR |
|---|---|---|---|
| 16 | (4-acetylphenyl)CH₂-(2-Br,6-Cl-phenyl)-triazinedione | 213~214 | [DMSO-d₆] 2.54(s, 3H), 4.42(s, 2H), 7.58(q, 4H), 7.70(s, 1H), 7.77(d, 1H), 7.89(d, 1H), 12.47(s, 1H). |
| 17 | (4-(2-hydroxypropan-2-yl)phenyl)CH₂-(2-Br,6-Cl-phenyl)-triazinedione | 118~120 | [CDCl₃] 1.57(s, 6H), 1.76(s, 1H), 4.38(s, 2H), 7.29(q, 4H), 7.59(s, 1H), 7.67(d, 1H), 7.80(d, 1H), 8.97(br, 1H). |
| 18 | (4-(1-(hydroxyimino)ethyl)phenyl)CH₂-(2-Br,6-Cl-phenyl)-triazinedione | 187~188 | [DMSO-d₆] 2.12(s, 3H), 4.35(s, 2H), 7.36(q, 4H), 7.70(s, 1H), 7.66(d, 1H), 7.88(d, 1H), 11.14(s, 1H), 12.46(s, 1H). |
| 19 | (4-acetylphenyl)CH₂-(2,6-diBr-phenyl)-triazinedione | 231~232 | [DMSO-d₆] 2.58(s, 3H), 4.49(s, 2H), 7.54(s, 1H), 7.56(q, 4H), 7.94(s, 2H), 12.40(s, 1H). |
| 20 | (4-(2-fluoropropan-2-yl)phenyl)CH₂-(2,6-diCl-phenyl)-triazinedione | 152~153 | [CDCl₃] 1.54(s, 3H), 1.78(s, 3H), 4.34(s, 2H), 7.17(d, 2H), 7.30(d, 2H), 7.58(s, 1H), 7.63(s, 2H), 8.69(br, 1H). |
| 21 | (6-(methylthio)pyridin-3-yl)CH₂-(2,6-diCl-phenyl)-triazinedione | 182~183 | [CDCl₃] 2.54(s, 3H), 4.27(s, 2H), 7.08(d, 1H), 7.36(dd, 1H), 7.58(s, 1H), 7.64(s, 2H), 8.36(d, 1H), 8.79(br, 1H). |
| 22 | (4-(1-chloro-2-hydroxypropan-2-yl)phenyl)CH₂-(2,6-diCl-phenyl)-triazinedione | caramelo | [CDCl₃] 1.61(br, 4H), 3.75(d, 2H), 4.34(s, 2H), 7.15~7.42(m, 4H), 7.58(s, 1H), 7.63(s, 2H), 8.66(br, 1H). |
| 23 | (4-(1-chloroethyl)phenyl)CH₂-(2,6-diCl-phenyl)-triazinedione | 142~143 | [CDCl₃] 1.82(d, 3H), 4.34(s, 2H), 5.07(q, 1H), 7.27(q, 4H), 7.60(s, 1H), 7.63(s, 2H), 8.63(br, 1H). |

TABLE 4

| No. | Structure | mp (°C) | NMR |
|---|---|---|---|
| 24 | 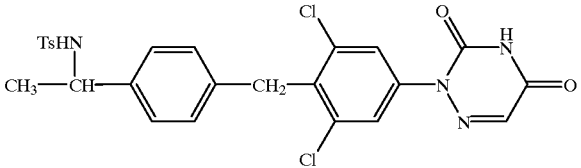 | 173~174 | [Acetone-d₆] 1.33(d, 3H), 2.35(s, 3H), 2.77(d, 1H), 4.31(s, 2H), 4.45(m, 1H), 6.83(s, 1H), 7.02~7.62(m, 9H), 7.77(s, 2H). |
| 25 | 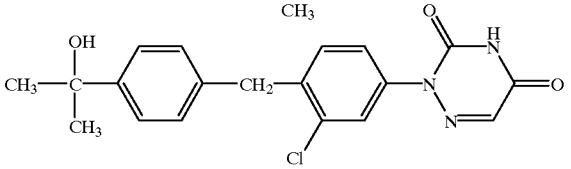 | 143~144 | [DMSO-d₆] 1.38(s, 6H), 2.29(s, 3H), 4.16(s, 2H), 4.90(br, 1H), 7.19(q, 4H), 7.36(s, 1H), 7.53(d, 1H), 7.66(d, 1H), 12.37(br, 1H). |
| 26 | 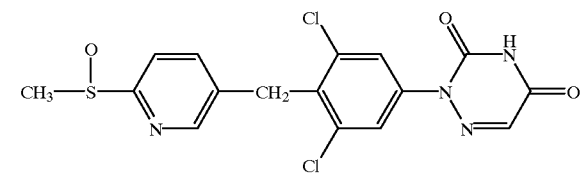 | 242~243 | [CDCl₃] 2.87(s, 3H), 4.40(s, 2H), 7.58(s, 1H), 7.68~7.79(m, 3H), 7.97(d, 1H), 8.56(d, 1H), 9.82(br, 1H). |
| 27 | 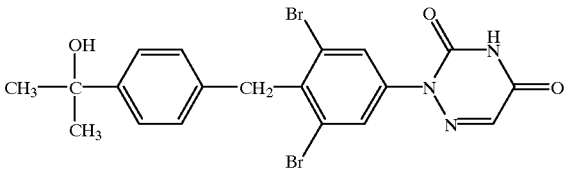 | | |
| 28 | 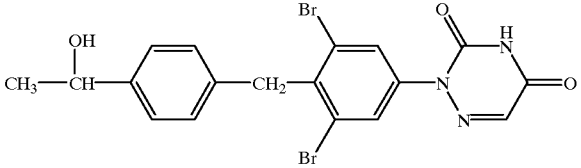 | | |

In Table 1 to 4, $^{iso}$Pro means isopropyl, Me means methyl, and Ts means tosyl.

In addition to the compounds listed in the above table, the following compounds, among others, can be mentioned as representative compound of the present invention.

(1) 4-Acetyl-2-[4-(4-acetylbenzyl)-3,5-dichlorophenyl]-1,2,4-triazine-3,5(2H,4H)-dione
(2) 2-[4-(4-Acetylbenzyl)-3,5-dichlorophenyl]-4-methyl-1,2,4-triazine-3,5(2H,4H)-dione
(3) 4-Acetyl-2-[3,5-dichloro-4-(4-α-hydroxyethylbenzyl)phenyl]-1,2,4-triazine-3,5(2H,4H)-dione
(4) 2-[3,5-dichloro-4-(4-α-hydroxyethylbenzyl)phenyl]-4-methyl-1,2,4-triazine-3,5(2H,4H)-dione Biological Tests Test Example 1

The potency of the compound of the present invention against coccidia was tested in chicks. Using 9-day-old male White Leghorn chicks in groups of 3, the birds in all the test groups other than an uninfected and untreated control group were orally inoculated with 5×10⁴ sporulating oocysts of a laboratory strain of *Eimeria tenella* per bird. As the test drug, the compound of the invention, dried and pulverized, was added to the standard ration (SDL No. 1, Nippon Formula Feed) at the level of 31.3 ppm and the medicated diet was given ad *libitum* for 9 days from 24 hours before infection to day 8 after infection. During the period, the chiks were weighed and bloody droppings were counted. In addition, the number of oocysts was determined for evaluation of anticoccidial efficacy.

The results are shown in Table 5.

TABLE 5

| Compound No. | Relative body weight gain (%)[1] | Number of bloody droppings[2] | OPG(log)[3] |
|---|---|---|---|
| Non-infected/treatment group | 100 | 0 | ND[4] |
| Infected/untreated control group | 33.0 | 9.0 | 6.0 |
| 1 | 103.4 | 0 | ND |
| 3 | 104.5 | 0 | ND |
| 4 | 106.5 | 0 | ND |

It is apparent from Table 5, as compared with the infected control group, the groups treated with the compound of the present invention showed increased body weight gains, indicating the excellent anticoccidial activity of the compound.

1) Relative body weight gain=

$$\frac{\text{Mean body weight gain in each test group}}{\text{Mean body weight gain in uninfected control group}} \times 100$$

2) Number of bloody droppings: The quantity of bloody stool discharged from the chick's intestinal canal was shown in the number of blood stains/bird on the litter on the peak day.
3) OPG: The number of oocysts excreted in each gram of stool (on day 7 after infection)
4) ND: not detected Formulation Example 1

2-{4-[4-(4-chlorobenzoyl)benzyl]-3,5-dichlorophenyl}-1,2,4-triazine-3,5(2H,4H)-dione (compound No. 1), 25 g, is weighed and pulverized to 100% under screen (355 μm) and mixed evenly with 975 g of rice bran and oil cake (1:1).

We claim:
1. A compound represented by the formula:

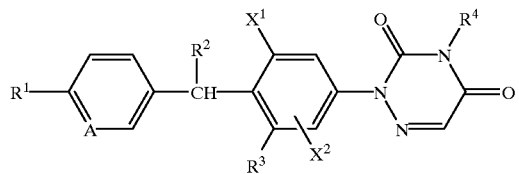

wherein $R^1$ is (1) an optionally substituted alkyl group, (2) an optionally substituted mono- or di-alkylanino group, (3) an optionally substituted alkoxy group, (4) an optionally substituted alkylsulfinyl group, (5) an optionally substituted alkylsulfonyl group, (6) an optionally substituted alkylthio group, (7) an optionally substituted acyl group selected from the group consisting of an alkanoyl group, a cycloalkyl-carbonyl group, an aryl-carbonyl group and an aralkyl-carbonyl group or (8) an optionally substituted sulfamoyl group;

A is —N= or —CH=;

$R^2$ is (1) a hydrogen atom, (2) a $C_{1-3}$ alkyl group which may optionally be substituted with halogen, (3) a $C_{1-3}$ alkoxy group, (4) a $C_{1-3}$ alkylthio group or (5) a mono- or di-$C_{1-3}$ alkyl) amino group;

$X^1$ is halogen or a lower alkyl group;

$X^2$ is a hydrogen atom or a fluorine atom;

$R^3$ is a hydrogen atom, halogen or a lower alkyl group; and $R^4$ is (1) a hydrogen atom, (2) an optionally substituted alkyl group or (3) an optionally substituted acyl group selected from the group consisting of a $C_{1-4}$ alkanoyl group and benzoyl group, provided that when $R^1$ is (1) a $C_{1-4}$ alkanoyl group, (2) benzoyl, (3) trifluoroacetyl, (4) sulfamoyl which may optionally be substituted with $C_{1-4}$ alkyl, (5) a $C_{1-4}$ alkyl group which may optionally be substituted with hydroxy, halogen or $C_{1-3}$ alkoxy, or (6) an amino group which is substituted with $C_{1-4}$ alkyl, A is —CH=, $R^2$ is a hydrogen atom, $X^1$ is a chlorine atom, $R^3$ is a chlorine atom, and $X^2$ is a hydrogen atom, then $R^4$ is (1) an optionally substituted alkyl group or (2) an optionally substituted acyl group selected from the group consisting of a $C_{1-4}$ alkanoyl group and benzoyl group; or a salt thereof.

2. The compound as claimed in claim 1, which is represented by the formula:

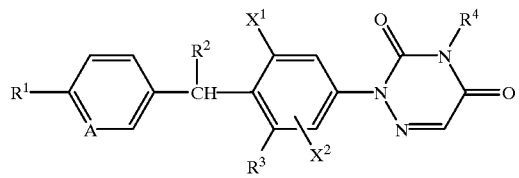

wherein $R^1$ is (1) an alkyl group which is substituted with (i) aryl, (ii) alkylidene, (iii) mercapto which may optionally be substituted, (iv) imino which may optionally be substituted or (v) amino which may optionally be substituted, or (2) a group of the formula: $R^8$—S(O)n—
wherein $R^8$ is an alkyl group and n is 1 or 2;

A is —N= or —CH=;

$R^2$ is (1) a hydrogen atom (2) a $C_{1-3}$ alkyl group which may optionally be substituted with halogen, (3) a $C_{1-3}$ alkoxy group, (b 4) a $C_{1-3}$ alkylthio group or (5) a mono- or di-($C_{1-2}$ alkyl) amino group;

$X^1$ is a halogen atom or a lower alkyl group;

$X^2$ is a hydrogen atom or a fluorine atom;

$R^3$ is a hydrogen atom, a halogen atom or a lower alkyl group; and $R^4$ is (1) a hydrogen atom, (2) an optionally substituted alkyl group or (3) an optionally substituted acyl group selected from the group consisting of a $C_{1-4}$ alkanoyl group and benzoyl group; or a salt thereof.

3. The compound as claimed in claim 2, wherein $R^1$ is (1) a $C_{1-7}$ alkyl group which is substituted with (i) $C_{6-14}$ aryl, (ii) $C_{1-3}$ alkylidene, (iii) mercapto which may optionally be substituted with a $C_{1-3}$ alkyl group, (iv) imino which may optionally be substituted with a hydroxy group or a $C_{1-4}$ alkoxy group, or (v) phenylsulfonylamino which may optionally be substituted with $C_{1-3}$ alkyl, (2) a $C_{1-4}$ alkylthio group, (3) a $C_{1-4}$ alkylsulfonyl group, or (4) a $C_{1-4}$ alkylsulfinyl group; A is —N= or —CH=; $R^2$ is a hydrogen group; $X^1$ is a halogen atom; $X^2$ is a hydrogen atom; $R^3$ is a halogen atom; and $R^4$ is a hydrogen atom; or a salt thereof.

4. The compound as claimed in claim 2, which is 2-{3,5-dichloro-4-[4-(propen-2-yl)benzyl]phenyl}-1,2,4-triazine-3,5(2H,4H)-dione or 2-{3,5-dichloro-4-[4-(1-tosylaminoethyl)benzyl]phenyl}-1,2,4-triazine-3,5(2H,4H)-dione; or a salt thereof.

5. The compound as claimed in claim 1, which is represented by the formula:

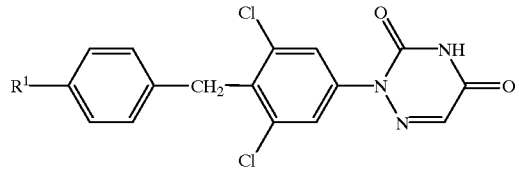

wherein $R^1$ is (1) a benzoyl group which is substituted with halogen, (2) a halogenated alkyl group which may optionally be substituted with hydroxy, (3) an alkanoyl group which is substituted with halogen or (4) an alkoxy group; or a salt thereof.

6. The compound as claimed in claim 5, wherein $R^1$ is (1) a benzoyl group which is substituted with halogen, (2) a halogenated $C_{1-4}$ alkyl group which may optionally be substituted with hydroxy, (3) a $C_{1-4}$ alkanoyl group which is substituted with halogen, or (4) a $C_{1-4}$ alkoxy group; or a salt thereof.

7. The compound as claimed in claim 5, which is 2-{3,5-dichloro-4-[4-(1-fluoro-1-methylethyl)benzyl]phenyl}-1,2,4-triazine-3,5(2H,4H)-dione or 2-{4-[4-(α-chloromethyl-α-hydroxyethyl)benzyl]-3,5-dichlorophenyl}-1,2,4-triazine-3,5(2H,4H)-dione; or a salt thereof.

8. The compound as claimed in claim 1, which is represented by the formula:

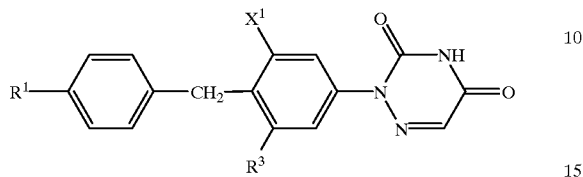

wherein $R^1$ is (1) an alkyl group which may optionally be substituted with hydroxy or (2) an alkanoyl group;

$X^1$ is a lower alkyl group or a bromine atom; and $R^3$ is a lower alkyl group or a halogen atom; or a salt thereof.

9. The compound as claimed in claim 8, wherein $R^1$ is (1) a $C_{1-4}$ alkyl group which may optionally be substituted with hydroxy or (2) a $C_{1-4}$ alkanoyl group; or a salt thereof.

10. The compound as claimed in claim 8, wherein $R^1$ is a $C_{1-4}$ alkyl group which is substituted with hydroxy, or a salt thereof.

11. The compound as claimed in claim 8, which is 2-{3-bromo-5-chloro-4-[4-(1-hydroxy-1-methylethyl)benzyl]phenyl}-1,2,4-triazine-3,5(2H,4H)-dione, 2-{3-chloro-4-[4-(1-hydroxy-1-methylethyl)benzyl]-3-methylphenyl}-1,2,4-triazine-3,5(2H,4H)-dione, 2-{3,5-dibromo-4-[4-(1-hydroxy-1-methylethyl)benzyl]phenyl}-1,2,4-triazine-3,5(2H,4H)-dione or 2-{3,5-dibromo-4-[4-(1-hydroxyethyl)benzyl]phenyl}-1,2,4-triazine-3,5(2H,4H)-dione; or a salt thereof.

12. The compound as claimed in claim 1, which is represented by the formula:

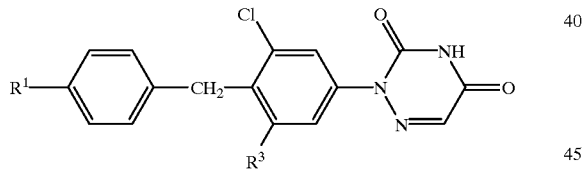

wherein $R^1$ is a $C_{1-4}$ alkanoyl group, and $R^3$ is a lower alkyl group; or a salt thereof.

13. The compound as claimed in claim 12, which is 2-[4-(4-acetylbenzyl)-3-chloro-5-methylphenyl]-1,2,4-triazine-3,5(2H,4H)-dione or a salt thereof.

14. 2-{3,5-Dichloro-4-[4-(1-hydroxy-1-methylethyl)benzyl]phenyl}-1,2,4-triazine-3,5(2H,4H)-dione or a salt thereof.

15. An antiprotozoal composition comprising an effective amount of the compound as claimed in claim 1 or a salt thereof, and a pharmaceutical acceptable carrier, excipient or diluent.

16. An antiprotozoal composition comprising an effective amount of the compound as claimed in claim 14 or a salt thereof, and a pharmaceutical acceptable carrier, excipient or diluent.

17. A method for producing of the compound as claimed in claim 1, which comprises:

(a) subjecting a compound of the formula:

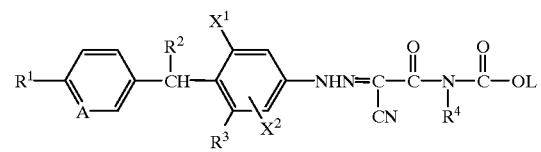

wherein L is a hydrogen atom, a $C_{1-3}$ alkyl group or an aryl group, and the other symbols have the same meaning as defined in claim 1, or a salt thereof to a cyclization reaction, a hydrolysis reaction of cyano, and a decarboxylation reaction to provide a compound of the formula:

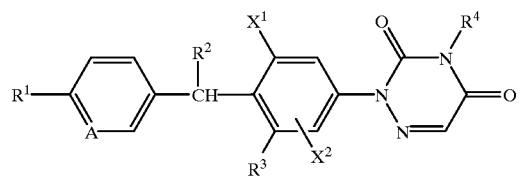

wherein each symbol has the same meaning as defined in claim 1; or a salt thereof, or (b) subjecting a compound of the formula:

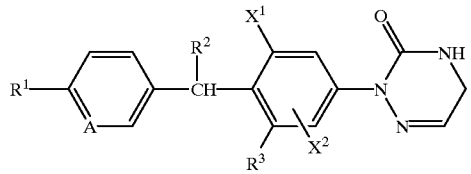

wherein each symbol has the same meaning as defined in claim 1; or a salt thereof to an oxidatioeaction to provide a compound of the formula:

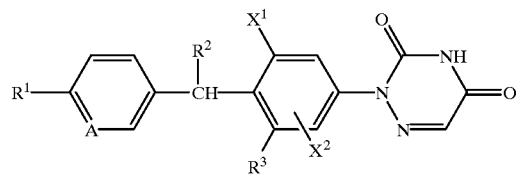

wherein each symbol has the same meaning as defined in claim 1; or a salt thereof, and if necessary, (c) reacting the resulting compound as claimed in claim 1 wherein $R^4$ is a hydrogen atom, or a salt thereof, with an acylating agent or an alkylating agent to provide the compound as claimed in claim 1 wherein $R^4$ is an optionally substituted alkyl group or an optionally substituted acyl group selected from the group consisting of a $C_{1-4}$ alkanoyl group and benzoyl group, or a salt thereof.

18. A method for preventing or treating a protozoal infection in a vertebrate or an insect which comprises administering an effective amount of the antiprotozoal composition as claimed in claim 15, to the vertebrate or insect.

* * * * *